United States Patent
Yoon et al.

(10) Patent No.: US 10,321,835 B2
(45) Date of Patent: Jun. 18, 2019

(54) BIOLOGICAL RECORDING DEVICE AND METHOD FOR RECORDING BIOLOGICAL ELECTRICAL ACTIVITY

(71) Applicant: The Regents of The University of Michigan, Ann Arbor, MI (US)

(72) Inventors: Euisik Yoon, Ypsilanti, MI (US); Sung-Yun Park, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 410 days.

(21) Appl. No.: 15/132,646

(22) Filed: Apr. 19, 2016

(65) Prior Publication Data
US 2017/0296080 A1  Oct. 19, 2017

(51) Int. Cl.
*A61B 5/0478* (2006.01)
*A61B 5/04* (2006.01)
*A61B 5/00* (2006.01)

(52) U.S. Cl.
CPC ........ *A61B 5/04012* (2013.01); *A61B 5/0478* (2013.01); *A61B 5/7203* (2013.01); *A61B 5/7228* (2013.01); *A61B 5/7242* (2013.01); *A61B 2560/0475* (2013.01); *A61B 2562/046* (2013.01)

(58) Field of Classification Search
CPC . A61B 5/04012; A61B 5/0478; A61B 5/7203; A61B 5/7228; A61B 5/7242; A61B 2560/0475; A61B 2562/046
USPC ................................................ 600/544, 545
See application file for complete search history.

(56) References Cited

U.S. PATENT DOCUMENTS

| | | | | |
|---|---|---|---|---|
| 7,361,188 B2* | 4/2008 | Barr | ..................... | A61B 5/0006 600/509 |
| 7,474,914 B2* | 1/2009 | Barr | ..................... | A61B 5/0404 600/509 |
| 7,896,807 B2* | 3/2011 | Clancy | ..................... | A61B 5/04 600/300 |
| 8,742,963 B2* | 6/2014 | Zou | ..................... | H03M 1/1215 341/141 |
| 8,958,868 B2* | 2/2015 | Ghovanloo | .......... | A61B 5/0031 600/544 |

(Continued)

OTHER PUBLICATIONS

Chae, Moo Sung et. al., A 128-Channel 6 mW Wireless Neural Recording IC with Spike Feature Extraction and UWB Transmitter, IEEE Transactions on Neural Systems and Rehabilitation Engineering, vol. 17, No. 4, Aug. 2009, pp. 312-321.

(Continued)

*Primary Examiner* — Navin Natnithithadha
(74) *Attorney, Agent, or Firm* — Reising Ethington P.C.

(57) ABSTRACT

A biological recording device used to monitor biological electrical activity and a method of recording neural signals. In a preferred embodiment, the biological recording device is a neural probe. The biological recording device includes a probe body with a probe shank and a recording platform that uses a delta ($\Delta$) modulator and a delta sigma analog to digital converter ($\Delta\Sigma$ ADC). The $\Delta$ modulator and the $\Delta\Sigma$ ADC form a $\Delta$-$\Delta\Sigma$ analog front end (AFE) architecture for processing biological electrical activity. A large dynamic range (DR) of neural signals, including local field potentials (LFPs) and action potentials (APs) for example, can be compressed and subsequently reconstructed.

19 Claims, 22 Drawing Sheets

(56) References Cited

U.S. PATENT DOCUMENTS

| | | | | |
|---|---|---|---|---|
| 2006/0173364 A1* | 8/2006 | Clancy | ................... | A61B 5/04 |
| | | | | 600/485 |
| 2006/0229521 A1* | 10/2006 | Barr | ................... | A61B 5/0006 |
| | | | | 600/509 |
| 2006/0229522 A1* | 10/2006 | Barr | ................... | A61B 5/0006 |
| | | | | 600/509 |
| 2006/0229523 A1* | 10/2006 | Barr | ................... | A61B 5/0404 |
| | | | | 600/509 |
| 2006/0229525 A1* | 10/2006 | Barr | ................... | A61B 5/0006 |
| | | | | 600/523 |
| 2009/0299207 A1* | 12/2009 | Barr | ................... | A61B 5/0006 |
| | | | | 600/523 |
| 2013/0226527 A1* | 8/2013 | Gore | ................... | A61B 5/7207 |
| | | | | 702/190 |
| 2013/0289522 A1* | 10/2013 | Musallam | ........... | A61M 5/1723 |
| | | | | 604/503 |
| 2014/0114616 A1* | 4/2014 | Lee | ................... | A61B 5/0428 |
| | | | | 702/190 |
| 2016/0354041 A1* | 12/2016 | Gore | ................... | A61B 5/7207 |
| 2017/0113053 A1* | 4/2017 | Brisben | .............. | A61B 5/04011 |
| 2017/0156617 A1* | 6/2017 | Allavatam | ......... | A61B 5/04017 |

OTHER PUBLICATIONS

Liew, Wen-Sin et. al., A 1-V 60-μW 16-Channel Interface Chip for Implantable Neural Recording, IEEE 2009 Custom Intergrated Circuits Conference (CICC), Department of Electrical and Computer Engineering, National University of Singapore, pp. 507-510.

\* cited by examiner

BIOLOGICAL RECORDING DEVICE AND METHOD FOR RECORDING BIOLOGICAL ELECTRICAL ACTIVITY

TECHNICAL FIELD

This invention relates generally to biological recording devices for monitoring biological electrical activity, and more particularly, to processing neural signals and other biological electrical signals.

BACKGROUND

For comprehensive neuroscience research and related applications such as brain-computer-interfaces or brain-machine-interfaces (BCI or BMI), neuroprosthetics, etc., it is advantageous to provide simultaneous monitoring over a large number of channels in a small volume while maintaining high signal quality to help provide an in-depth understanding of brain activities. However, to facilitate a large number of parallel recordings with high electrical performance, both power and area consumptions inevitably increase dramatically, and therefore it has been recognized as one of the biggest challenges to overcome in neural multi-channel recordings and related applications. While some have attempted to achieve this goal, no previous approach has fully addressed both area and energy efficiency simultaneously to achieve massively-parallel multi-channel recordings.

Conventional approaches that attempt to effectively use area and energy typically use channel multiplexing and a successive approximation register analog-to-digital converter (SAR-ADC) as a quantizer in the recordings since there is no static power consumption in SAR-ADC and the switching power of the SAR-ADC can be significantly reduced by using smaller size capacitors and some special control schemes. Channel multiplexing is used sometimes as a compromising solution for the area reduction since the SAR-ADC consumes a relatively large area compared with other types of ADCs. However, channel multiplexing has serious shortcomings. The multiplexing itself needs high-speed buffers and switches which lead to additional power consumption. Additionally, the quality of the recording might be deteriorated since crosstalk between channels may occur. High-quality recording requiring more than 60 dB dynamic range (DR) can be affected by this crosstalk since modern CMOS switches only provide a few $G\Omega$ range off-resistance.

SUMMARY

According to one embodiment, there is provided a biological recording device comprising a probe body having a probe shank, a plurality of recording electrodes on the probe shank for monitoring biological electrical activity, and a recording platform attached to the probe body for processing the biological activity monitored by the plurality of recording electrodes. The recording platform includes a delta ($\Delta$) modulator, and the dynamic range of the biological electrical activity is modulated by the $\Delta$ modulator.

According to another embodiment, there is provided a biological recording device comprising a probe body having a probe shank, a plurality of recording electrodes on the probe shank for monitoring biological electrical activity, and a recording platform attached to the probe body for processing the biological activity monitored by the plurality of recording electrodes. The recording platform includes a delta sigma analog-to-digital converter ($\Delta\Sigma$ ADC) to digitize the biological electrical activity.

According to another embodiment, there is provided a method of processing neural signals. The method comprises the steps of acquiring a dynamic range for a plurality of neural signals, compressing the dynamic range for the plurality of neural signals, and quantizing the compressed dynamic range for the plurality of neural signals using a delta sigma analog-to-digital converter ($\Delta\Sigma$ ADC).

BRIEF DESCRIPTION OF THE DRAWINGS

Preferred exemplary embodiments will hereinafter be described in conjunction with the appended drawings, wherein like designations denote like elements, and wherein.

DETAILED DESCRIPTION OF THE ILLUSTRATED EMBODIMENTS

Figure 1:
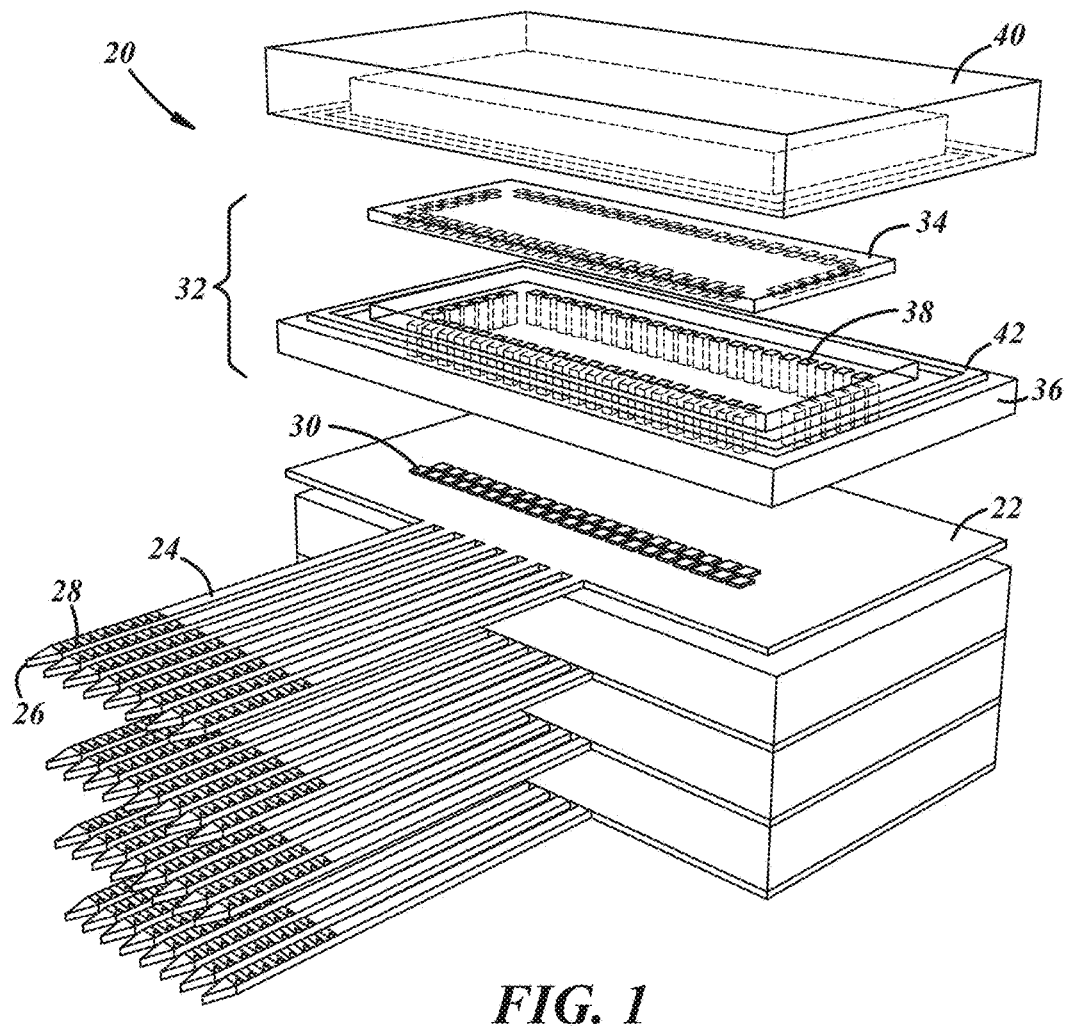
FIG. 1 is a partial, segmented view of a biological recording device.

The biological recording device and method disclosed herein allow for massively parallel recordings with a very small energy-area product which can indicate how efficiently the area and energy are used for implementing the recording electronics. Moreover, particularly with respect to neural signal processing, a wide dynamic range (DR) of signals can be processed without sacrificing signal integrity. The recording device and method, according to one embodiment, involves an energy-efficient and area-efficient modular analog front end (AFE) architecture that incorporates delta-modulated, delta-sigma (Δ-ΔΣ) signal acquisition. To save energy, Δ-modulation may be used to compress, and thereby reduce the variation in, the DR of neural signals. This may be accomplished by taking a temporal difference of oversampled signals instead of recording raw signals. "Oversampling" or "oversampled" as used herein generally means high sampling, or more than the Nyquist rate, though other rates may certainly be used. Oversampling works advantageously with monitoring brain activity because of the nature of neural signals, which have most of their energy at low frequencies and follow a ~1/f curve in their signal spectrum. For quantization, ΔΣ ADCs can be employed since they are more compact than successive approximation register (SAR) ADCs, which are often implemented with over 10-bit resolution. In other words, SAR-ADCs can generate output digital codes with charge sharing in binary weighted capacitors. Thus, as the required resolution is increased, the area consumption is exponentially increased, resulting in a huge area consumption in multi-channel AFEs. The implementation of ΔΣ ADCs can significantly reduce area, while their energy overhead can be compensated by the DR compression scheme. In one embodiment, continuous time (CT) operation of a Δ-ΔΣ ADC can help save energy due to its small bandwidth requirement.

To understand brain activity, both local field potentials (LFPs) and action potentials (APs or spikes) should be monitored simultaneously. The amplitudes of these signals range from the order of a few μV to several mV and their respective frequencies span from DC to a few kHz. LFPs, which represent an ensemble of the activity from the sets of neurons that surround the recording electrodes, can be found in the low-frequency range (e.g., about 1 Hz to about 300 Hz). On the other hand, APs, which represent single-cell activity, are located in a higher frequency range (e.g., about 300 Hz to about 10,000 Hz). According to the nature of LFPs and APs, recording circuits are advantageously designed with sufficiently low input-referred noise and high gain and dynamic range (DR) to encompass both LFPs and APs simultaneously. Furthermore, large DC fluctuations coming from the electrode-tissue interface can exist in the input signals and have to be removed by high-pass filtering at very low cutoff frequencies. Thus, it is preferable if the AFE facilitates certain instrument level performance parameters such as over 60 dB DR, less than 5 μV input referred noise (IRN), and more than 40 dB gain (preferably variable), which consequently results in large energy and area consumption for many devices.

With the biological recording devices described herein, high-quality, parallel monitoring over a large number of channels in a small volume of tissue can provide in-depth understanding of biological activity, particularly with respect to brain and neural activity. More specifically, in an embodiment, it is possible to achieve greater than 10-bit resolution with only 3.05 μW power consumption. In addition, a Δ-ΔΣ ADC can occupy a small area of about 40 μm×650 μm while enabling true parallel signal processing without any multiplexing scheme. Overall, the AFE architecture can achieve high energy-area efficiency while maintaining state-of-the-art low noise performance (e.g. more than 60 dB signal to noise ratio (SNR)) and facilitating a high enough DR to capture large swings of local field potentials (LFPs) without distortion. The energy-area product is typically considered the most critical figure of merit for massively-parallel recordings, and in one embodiment, the AFE architecture achieves 4.84 fJ/C-s*mm$^2$, the smallest ever reported.

Figure 2:
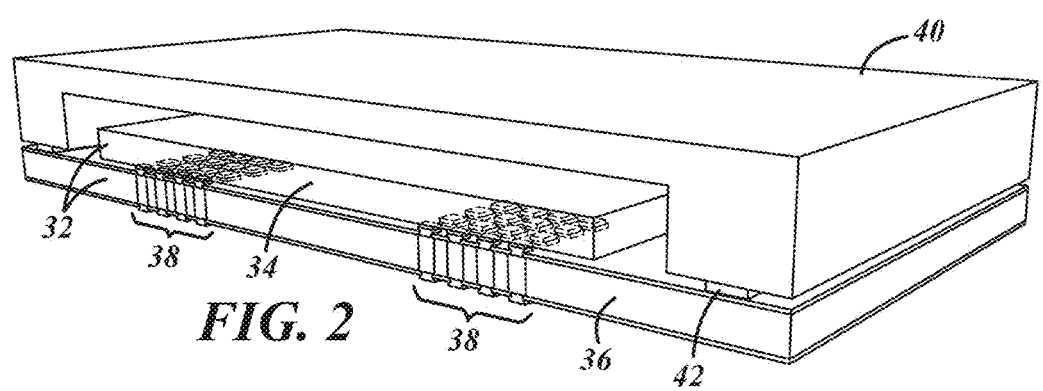
FIG. 2 is a cross sectional view of a recording platform for the biological recording device of FIG. 1.
Figure 3:
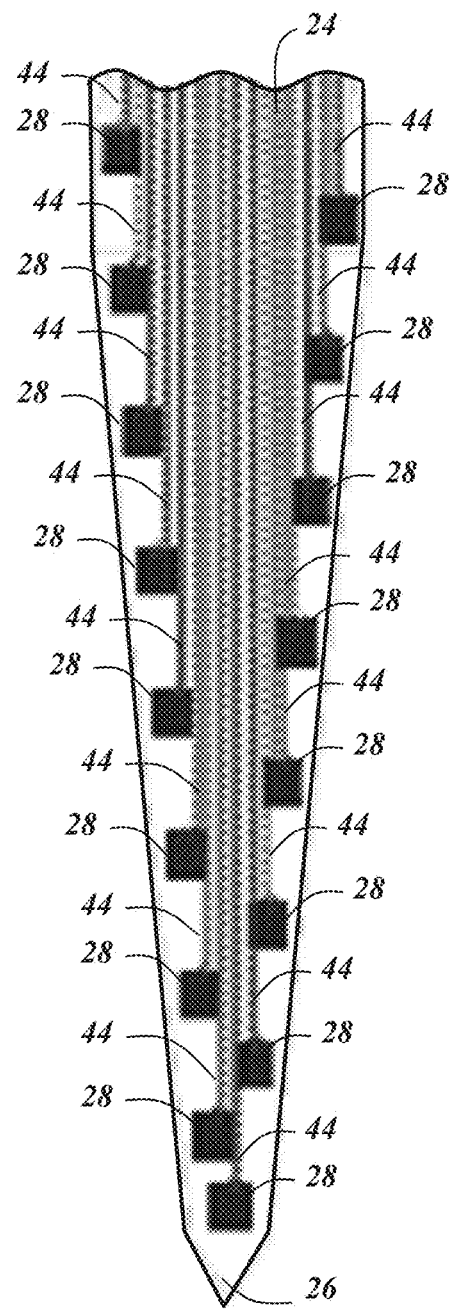
FIG. 3 is an enlarged view of an exemplary tip of a probe shank.

FIGS. 1-3 illustrate various aspects of biological recording devices according to particular embodiments. FIG. 1 is a partial, segmented view of a biological recording device 20. The biological recording device 20 is preferably used as a neural probe for recording neural signals. However, other biological implementations are certainly possible. The biological recording device 20 includes a probe body 22 having a plurality of probe shanks 24 that each extend from the probe body 22 to a corresponding tip 26. For clarity purposes, certain reference numerals are only shown in the segmented portion of the figure and to describe only one probe shank 24, but skilled artisans will recognize that the figure shows a plurality of respective parts. A plurality of recording electrodes 28 are located on the probe shank 24 for monitoring biological electrical activity. The probe body 22 includes a plurality of connection sites 30 that help facilitate signal transmission to other components of the biological recording device 20, such as a recording platform 32.

The recording platform 32 of the biological recording device 20 processes the biological electrical activity monitored by the plurality of recording electrodes 28. The recording platform 32 is attached, either directly or indirectly, to the probe body 22. The recording platform 32 includes an AFE architecture 34, which is described in detail below, and may include an interposer 36 which interconnects the AFE architecture 34 and the probe body 22. FIG. 2 is a cross sectional view of a recording platform 32 according to one embodiment. A number of through-silicon-vias (TSVs) 38 exist to allow for the AFE architecture 34 to be flip-chip bonded to the interposer 36, providing vertical interconnects between the AFE architecture 34 and the probe body 22. A silicon (Si) cap 40 may be used for hermetic sealing, to prevent leakage, and to assist in restricting electrical contact so that it is at least partially localized between the tissue and the recording electrodes 28. Additionally, an indium (In) sealing rim 42 for solder bonding may be used to help seal the various components of the recording platform 32.

In an embodiment, the biological recording device 20 includes eight probe bodies 22 and eight recording platforms 32 (only four of each are shown in FIG. 1). In the embodiment illustrated in FIG. 1, each probe body 22 includes eight probe shanks 24, and as can be seen in FIG. 3, each probe shank 24 may include sixteen recording electrodes 28. Each recording electrode 28 includes its own electrical connection or channel 44. Accordingly, in at least some embodiments, each probe body 22 has 128 channels, and with eight probe bodies, 1,024 channel parallel neural recording is possible. Dimensionally, in one implementation, each probe shank 24 is approximately 6 mm long and 15 μm thick with the recording electrodes spaced approximately 20 μm from each other along the length of the probe shank 24. The interposer 36 may be about 10.8 mm×5 mm×0.04 mm with approximately 135 through-silicon-vias 38. Other dimensions, configurations, numbers of probe bodies, probe shanks, and recording platforms are certainly possible. For example, the probe bodies with their respective recording platforms could be situated in a side-by-side scalable architecture instead of being stacked.

Figure 4:
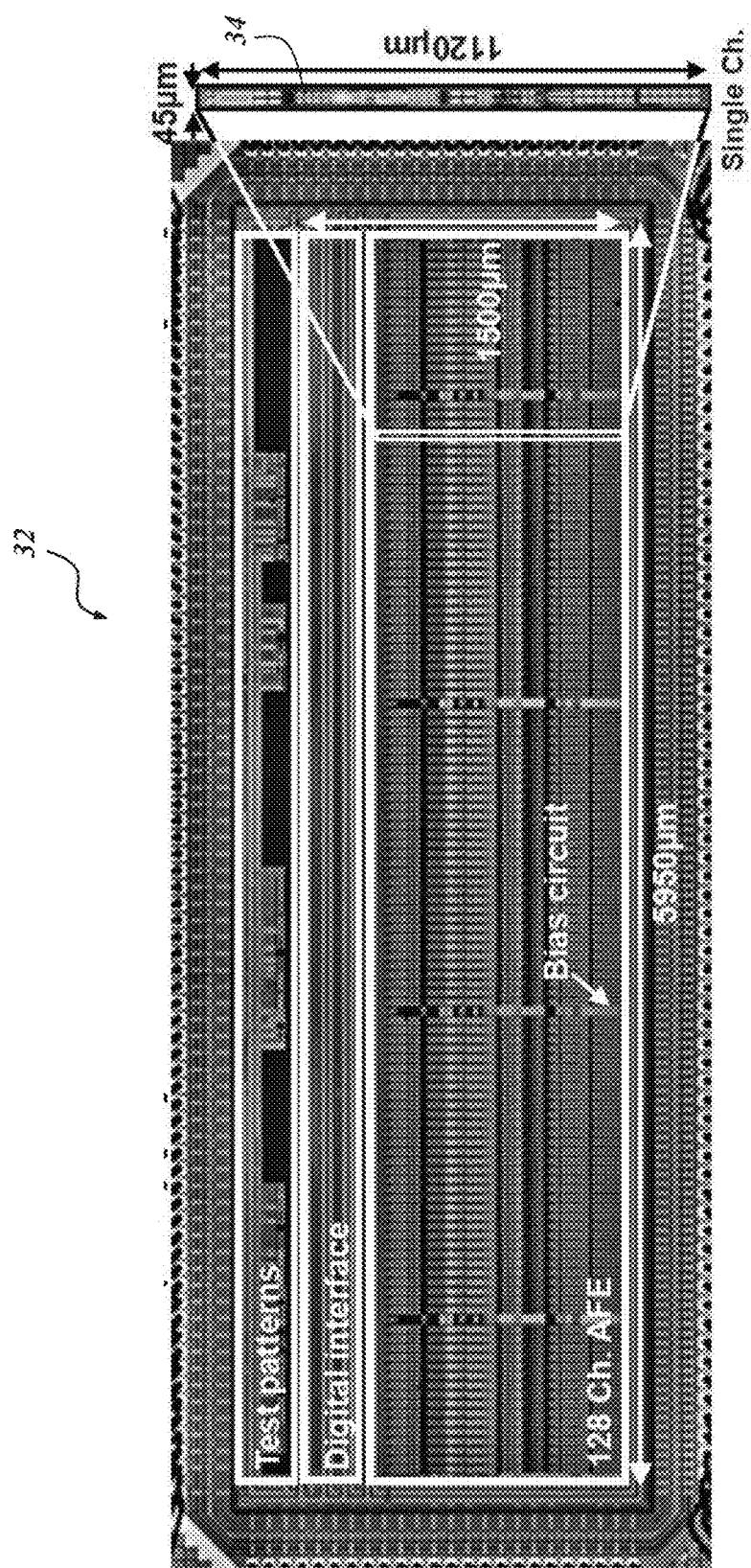
FIG. 4 is a die photo-micrograph of a fabricated recording platform.
Figure 5:
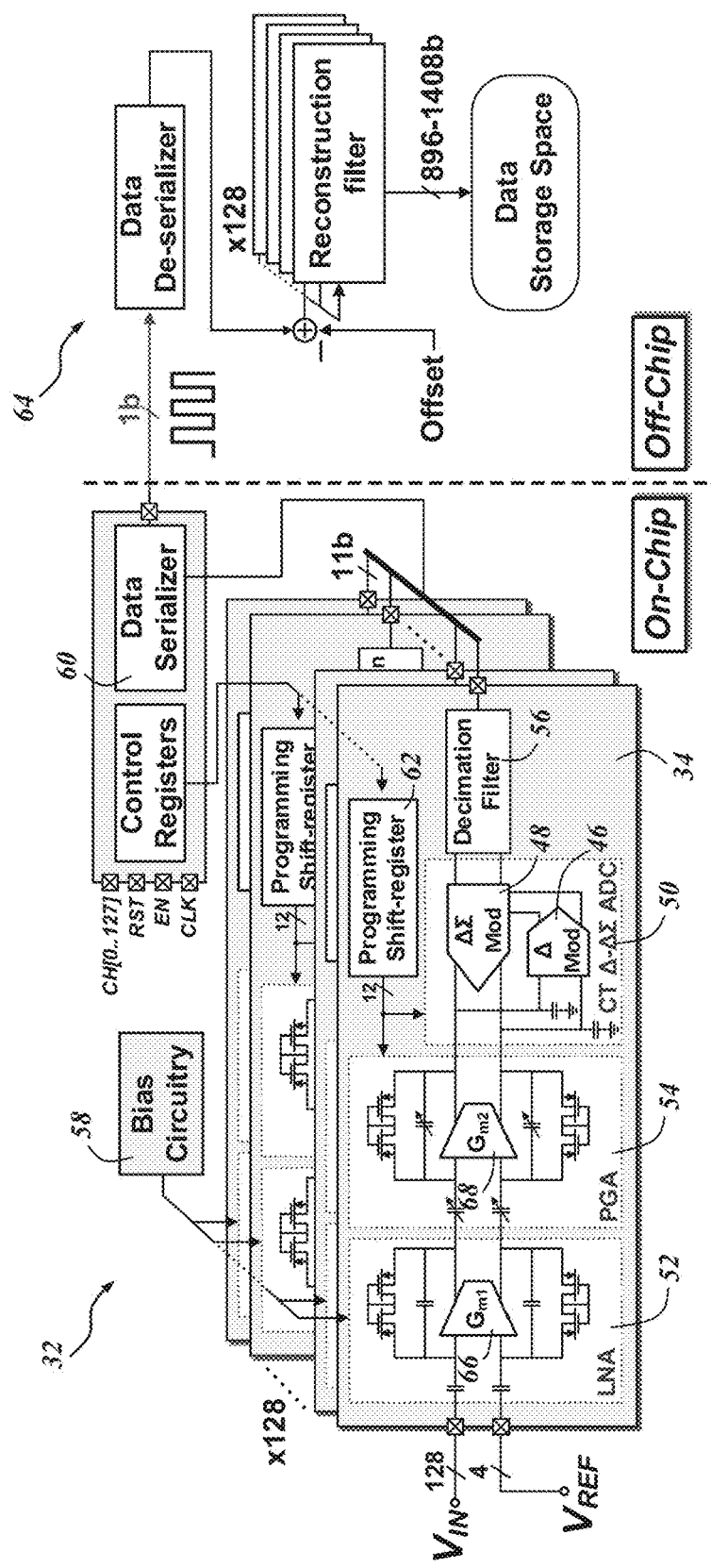
FIG. 5 is a schematic diagram of a 1,024-channel biological recording platform.

FIG. 4 is a die photo-micrograph of a fabricated recording platform 32 with a 128 channel AFE architecture 34, and FIG. 5 is a schematic diagram of one embodiment of an AFE architecture 34. Generally, "on-chip" in the figures represents components and processing on or integrated with the biological recording device 20, while "off-chip" represents components and processing remote from the biological recording device 20. However, it may be possible that some "off-chip" components and processing may be done "on-chip" and vice versa. In this particular embodiment, on-chip signal conditioning is accomplished through the Δ-modulated ΔΣ(Δ-ΔΣ) AFE 34 with a Δ-modulator 46 and a ΔΣ analog-to-digital converter (ADC) 48 which form a Δ-ΔΣ ADC 50. In this particular embodiment, the Δ-ΔΣ ADC 50 is operated in continuous time (CT) as opposed to discrete time. The on-chip AFE 34 consists of 128 signal acquisition channels, each including a low-noise amplifier (LNA) 52, a programmable gain amplifier (PGA) 54, the Δ-ΔΣ ADC 50, and a digital decimation filter 56 in series. Other connection arrangements and component combinations are certainly possible. Since all of the implemented channels are independent (e.g., consisting of a single LNA 52, PGA 54, and Δ-ΔΣ ADC 50 in each channel) the proposed architecture allows for the number of channels to be increased more efficiently than other AFE architectures where some of the channels are shared.

The AFE architecture 34 also includes bias circuits 58 and a data serializer 60 to support the data processing in the channels. Additionally, a programming shift register 62 may be included to change the gain and bandwidth setting of the LNA 52 and PGA 54. Other circuitry configurations and components are certainly possible. All of the amplified, modulated biological signals from the 128-channel Δ-ΔΣ AFE 34 can be serialized onto a single bit and sent to one or more off-chip modules 64 for signal restoration and storage. Since the incoming data are modulated, it is advantageous to process the signals to retrieve the original data. Accordingly, off-chip signal restoration may be performed in order to analyze the biological electrical activity.

Figure 6:
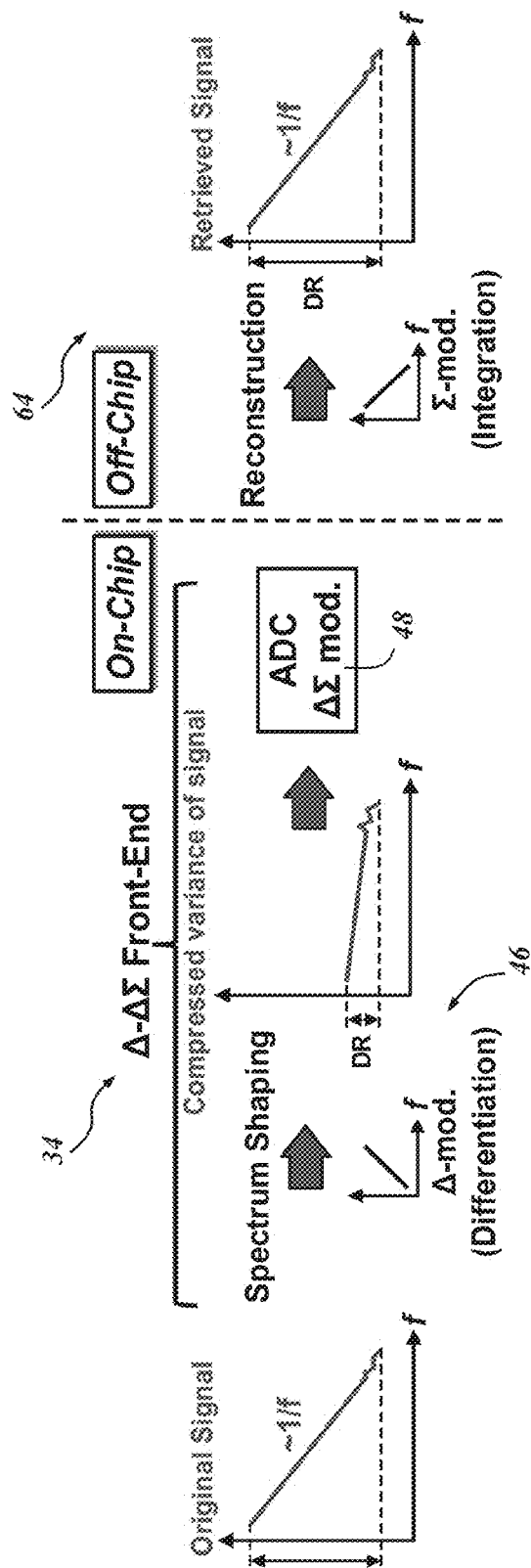
FIG. 6 shows graphical representations of biological electrical activity processing.

FIG. 6 shows graphical representations of biological electrical activity processing. The signal spectra conceptually illustrate the significant DR compression of neural signals by the Δ-modulator 46. The DR for a plurality of neural signals may be acquired by the biological recording device 20 itself, or an off-chip module 64, for example. "Acquiring" may include receiving, determining, calculating, obtaining, etc. a DR representative of a plurality of neural signals. The compressed signal can be digitized by the ΔΣ ADC 48 with reduced resolution requirements, and sent to the off-chip module 64 for remote processing. Remote from the recording platform, the compressed neural signal may be processed with Σ-modulation, for example, to retrieve the original signal.

Figure 7:
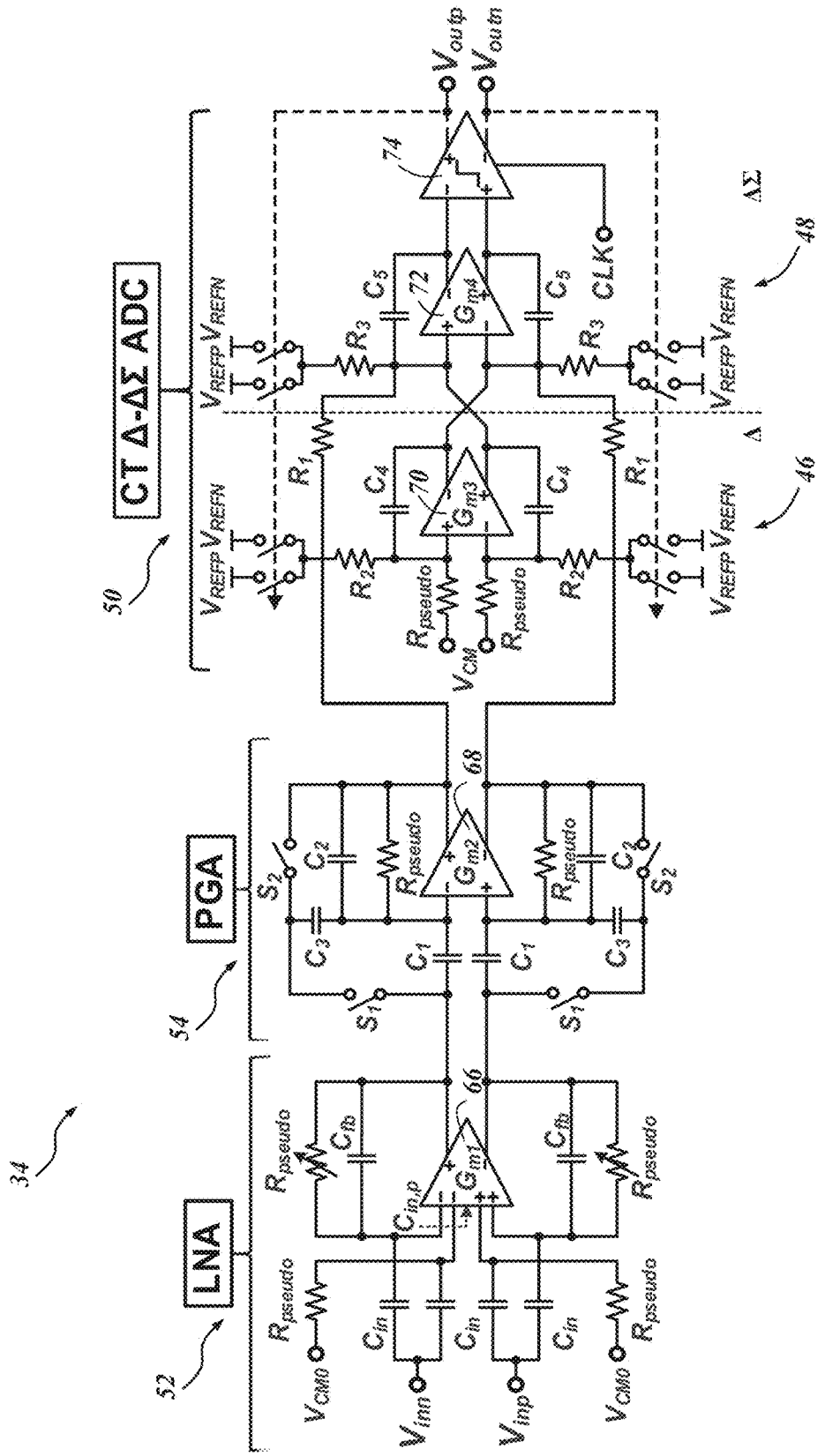
FIG. 7 is a schematic diagram of a single channel delta-modulated, delta-sigma analog-to-digital converter analog front end architecture ($\Delta$-$\Delta\Sigma$ ADC AFE)

FIG. 7 is a schematic of a single channel Δ-ΔΣ AFE architecture 34. The AFE architecture 34 can operate fully-differentially to minimize any common mode variations and increase the DR of signals. Because of the CT-operation of the Δ-ΔΣ ADC 50, no sample-and-hold (S/H) circuit between the PGA 54 and Δ-ΔΣ ADC 50 is necessary and the anti-aliasing requirement can also be relaxed. The analog blocks can be operated with a variable supply from about 0.5 V to 1.0 V. However, it is preferable for the comparator that is connected to digital blocks to be operated with a 1.0 V supply, which will be discussed in further detail below. The Δ-ΔΣ AFE 34 may consume only 3.05 μW power while occupying a small area of 0.05 mm² (45 μm×1120 μm). Parameters such as low- and high-frequency corner ($f_L$ and $f_H$) and total gain of the channel may be externally programmable.

The small area and energy consumption of the AFE architecture 34 can result in easier scalability, particularly because multiplexing is in the digital domain. While some prior art devices incorporate digital multiplexing, the scalability to a massive number of channels, such as the 1,024 channel implementation described herein, is limited since the area and energy consumption per channel is higher than the proposed architecture. Further, for analog multiplexing, a power consuming analog multiplexer is typically used. By increasing the number of the multiplexing ratio, the overall area consumption of the AFE is reduced, but the overall energy (e.g., power) consumption is increased. In certain implementations of the AFE architecture 34 described herein, the analog multiplexer is unnecessary since the multiplexing is done in the digital domain. Further, with an analog multiplexer, the signal in a channel can leak into adjacent channels since the sampling capacitor is typically shared by the different channels. However, in the device implementations proposed herein, channel leakage is minimized to the substrate of the die.

In the embodiment illustrated in FIG. 7, since the LNA 52 is located in the very first stage of the whole signal processing chain, it should provide enough gain for the following stages to process the input signals while exhibiting low noise performance. In addition, it is preferable if the LNA 52 rejects large DC fluctuations (e.g., about 50 to 100 mV) coming from the probe-tissue interface. In the LNA 52, input signals are capacitively coupled, or AC coupled, to a plurality of capacitors—four capacitors, $C_{in}$, in this embodiment—so that sub-Hz high pass corner frequency can be formed with $C_{in}$ and $R_{pseudo}$ to suppress the large DC fluctuation. $C_{in}$ should be made small enough to guarantee high input impedance at frequencies of interest to minimize signal attenuation from the probe, but large enough to avoid attenuation from the capacitive divider it forms with the transconductor $G_{m1}$ 66, or more particularly in this embodiment, an operational transconductance amplifier (OTA) which is illustrated in accordance with one embodiment in FIG. 8. This can increase input-referred noise, as shown in equation 1 below $$\overline{v_{ni}^2} = \left(\frac{C_{in} + C_{fb} + C_{in,p}}{C_{in}}\right) \cdot \overline{v_{ni,OTA1}^2} \quad \text{(equation 1)}$$

where $C_{in,p}$ is the parasitic input capacitance of $G_{m1}$, $\overline{v_{ni}^2}$, and $\overline{v_{ni,OTA1}^2}$ are the input referred noise of the LNA 52 and $G_{m1}$ 66 OTA1, respectively. The gain of the LNA 52 can be generated by the closed loop feedback by $C_{fb}$ and the ratio that $C_{in}$ to $C_{fb}$ makes to overall gain. In one particular implementation, $C_{in}$ and $C_{fb}$ are chosen to limit the input referred noise by the capacitive divider to be less than 10% while maintaining reasonable input impedance and closed loop gain. Even though large capacitors are used for the closed-loop gain and capacitive or AC coupling, area overhead may be conserved since they can be placed adjacent to, or more particularly on top of, the active circuitry. For implementation of the large resistor, $R_{pseudo}$, the leakage current from a lateral bipolar junction transistor and a PMOS transistor can be used. The input referred noise from $R_{pseudo}$ may be provided in accordance with equation 2 below:

$$\overline{v_{ni,R}^2} = \left(\frac{V_{n,R}}{1+sR_{pseudo}C_{fb}}\right) \cdot \left(\frac{1}{A^2}\right) \quad \text{(equation 2)}$$

where $V_{n,R}$ is the thermal noise of $R_{pseudo}$ and A is a 40 dB closed-loop gain of the LNA 52, respectively. According to equation 2, the input referred noise from $R_{pseudo}$ is largely attenuated by both A and the R-C network (−20 dB/dec) after sub-Hz frequency, $1/(2pR_{pseudo}C_{fb})$. Thus, the noise contribution from $R_{pseudo}$ is negligible compared to the thermal noise or flicker noise from $G_{m1}$ 66. The thermal noise density of $G_{m1}$ is given by equation 3 below:

$$\overline{v_{ni,th}^2} \approx \frac{8kT}{3} \cdot \left(\frac{1}{g_{m1}+g_{m3}}\right) \cdot \Delta f \quad \text{(equation 3)}$$

where k is the Boltzmann constant, T is absolute temperature, and $g_{m1}$ and $g_{m3}$ are the transconductance of $M_1$ and $M_3$, respectively.

Figure 8:
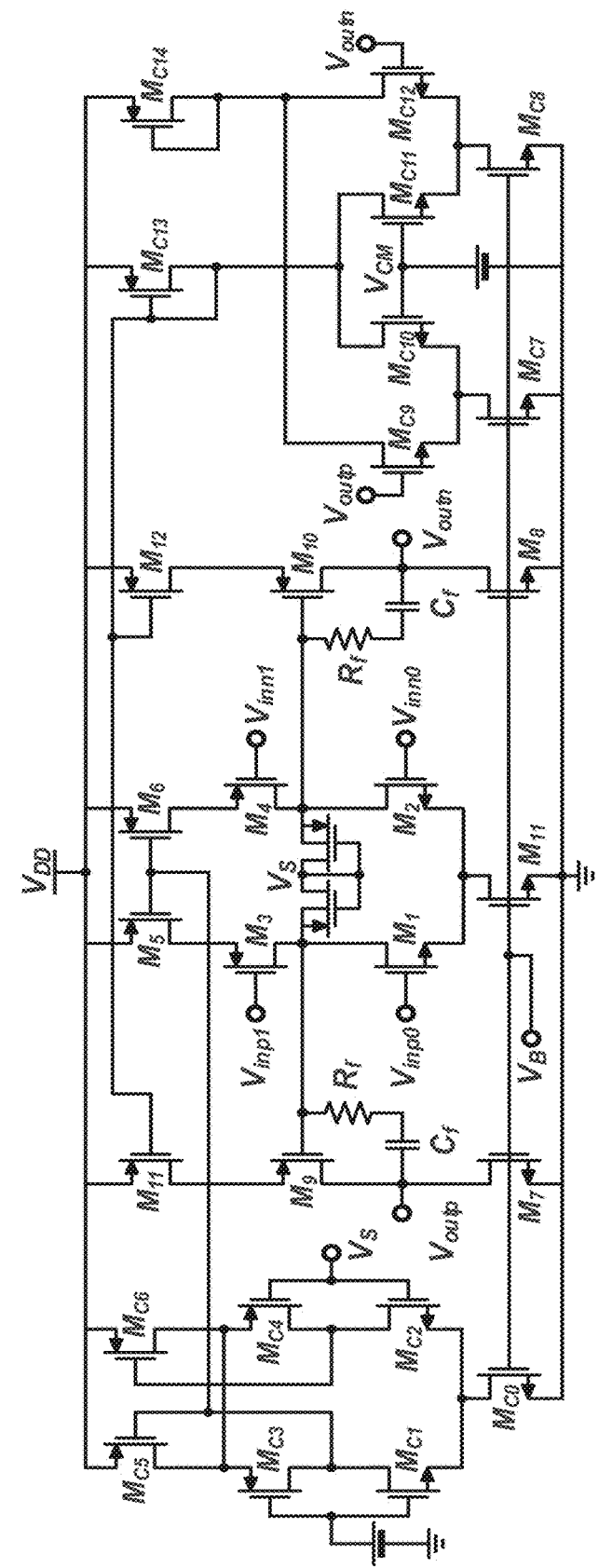
FIG. 8 is a schematic diagram of a transconductor $G_{m1}$ for a low noise amplifier (LNA)

To achieve low-noise performance of the LNA 52, all transistors in $G_{m1}$ 66 are preferably designed to operate in the subthreshold region where the transconductance efficiency is maximized. $G_{m1}$ 66 also has two complementary inputs ($M_1$-$M_4$) as depicted in FIG. 8. The complementary inputs increase the transconductance of the first stage by factor of two theoretically, and consequently reduce the input thermal noise by factor of $\sqrt{2}$ in accordance with equation 3. The input referred flicker noise of $G_{m1}$ 66 is also given by equation 4, below:

$$\overline{v_{ni,1/f}^2} \approx \frac{1}{C_{ox}} \cdot \left(\frac{K_n g_{m1}^2}{(WL)_1} + \frac{K_p g_{m3}^2}{(WL)_3}\right) \cdot \left(\frac{1}{g_{m1}+g_{m3}}\right)^2 \cdot \frac{1}{\Delta f} \quad \text{(equation 4)}$$

where $K_n$ and $K_p$ are flicker noise coefficients of the standard 1.8 V NMOS and PMOS, respectively. The large gate area of the input transistors can be used to reduce the flicker noise.

Due to a squeezed 0.5V supply voltage, a single DC voltage may not effectively provide the proper bias for both the NMOS ($M_1$ and $M_2$) and PMOS ($M_3$ and $M_4$) transistors. The input DC bias for $M_1$ and $M_2$ comes from the output common mode, $V_{CM}$, which is half of the supply voltage. The input DC bias for $M_3$ and $M_4$ can be generated using two diode connected PMOSs (not shown in FIG. 8). The squeezed supply voltage can also deteriorate the common mode rejection ratio (CMRR) and power supply rejection ratio (PSRR) of $G_{m1}$ 66. Accordingly, the dual tail currents ($M_0$, $M_5$, and $M_6$) can be used to reduce the common mode gain.

In the FIG. 8 embodiment, since $G_{m1}$ 66 has two amplification stages, a frequency compensation network should be used to guarantee enough phase margin. It is also preferable if each stage of the transconductor $G_{m1}$ 66 has common mode feedback (CMFB). Two schematics of two different CMFB circuits are provided in FIG. 8 as well. The transistors used for the CMFB circuits are indicated with a subscript "c" in FIG. 8. The LNA 52 can generate 3.32 $\mu V_{rms}$ input referred noise through 0.5 Hz to 12.7 kHz while consuming 1.6 $\mu$A static current. However, the power consumption of the LNA 52 remains at sub-$\mu$W levels due at least in part to the 0.5V supply. Figures of merit such as the noise efficiency factor (NEF) and $NEF^2V_{DD}$ (reflects the employed voltage supply) for the LNAs 52 are comparable or better when compared with other devices. For example, in one embodiment, the fabricated circuits consume 0.05 mm$^2$ and 3.05 $\mu$W per channel, exhibiting 63.8 dB SNDR, 3.02 NEF, and 4.56 $NEF^2V_{DD}$.

Figure 9:
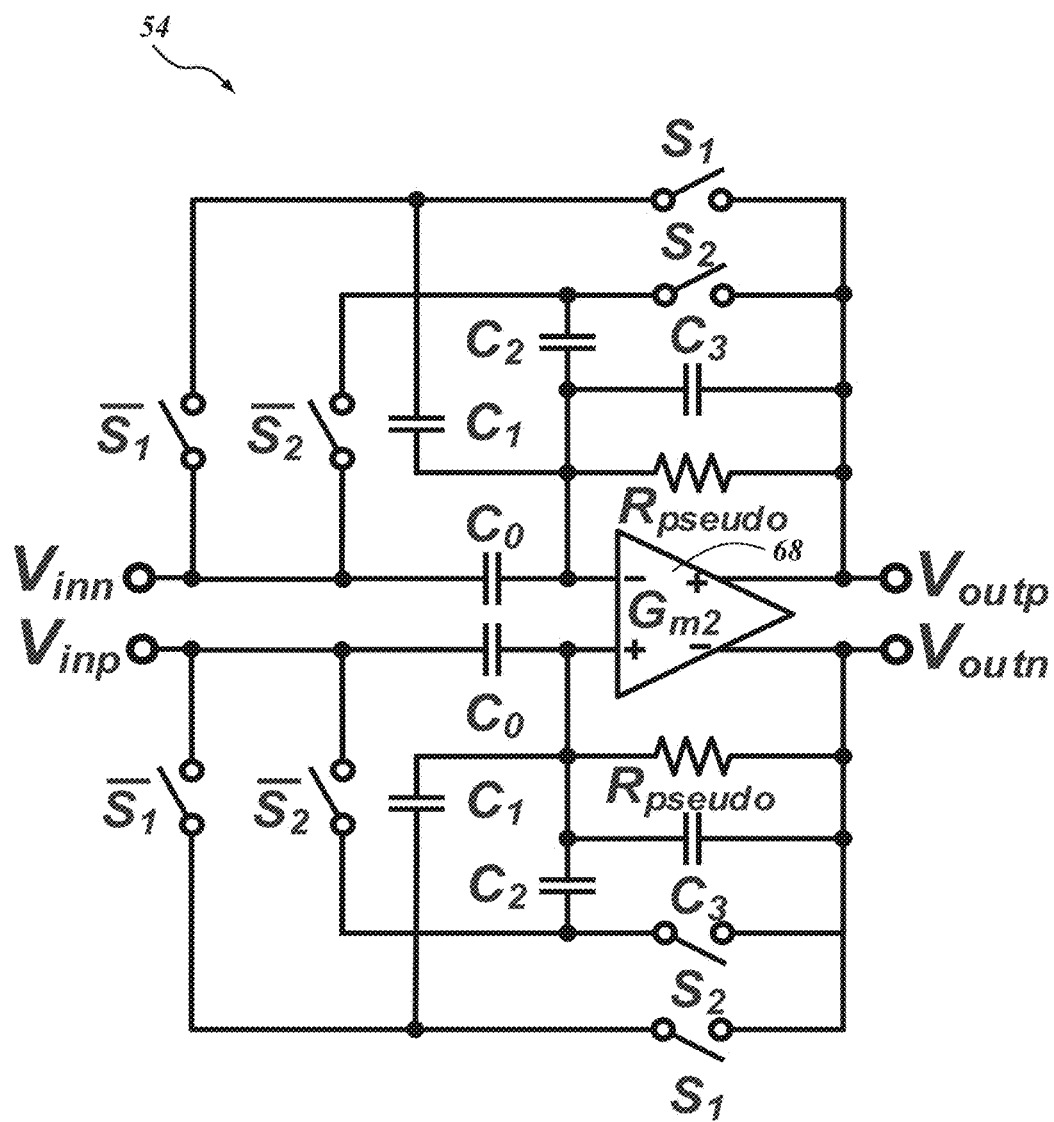
FIG. 9 is a schematic diagram of a programmable gain amplifier (PGA)
Figure 10:
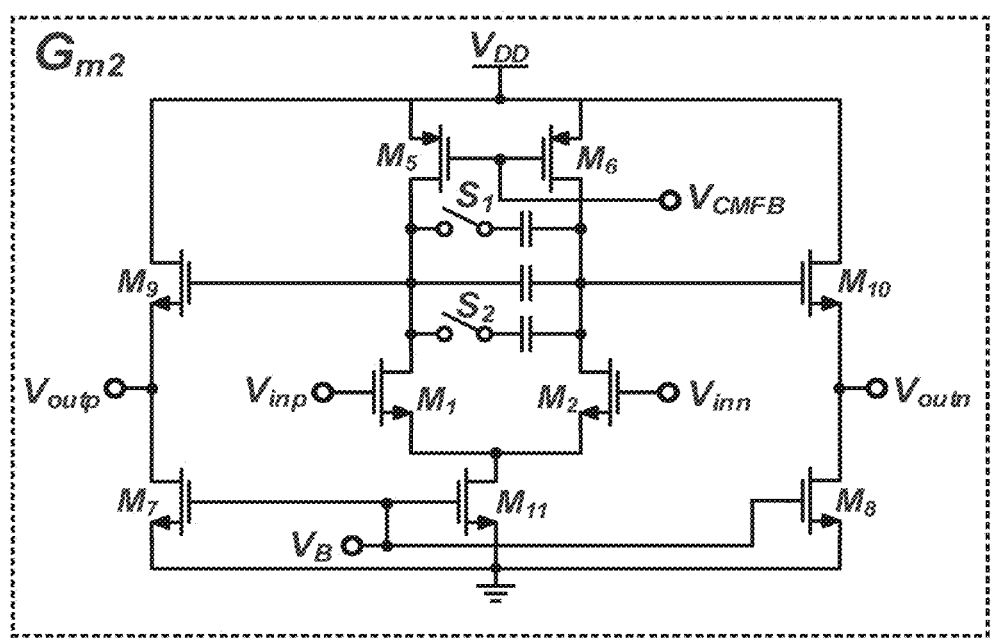
FIG. 10 is a schematic diagram of a transconductor $G_{m2}$ for the PGA of FIG. 9.

Returning to FIG. 7, between the LNA 52 and the Δ-ΔΣ ADC 50, a PGA 54 is inserted to provide more gain and to drive the following Δ-ΔΣ ADC 50. FIG. 9 is a schematic of the PGA 54, and FIG. 10 is a schematic of the PGA's transconductor $G_{m2}$ 68. The voltage gain of the PGA 54 can be adjusted by varying its feedback factor using the two switches $S_1$ and $S_2$ as shown in FIG. 10. Conventionally, a common approach for the gain adjustment can cause signal distortion at very low frequencies due to the reactance from the off-state resistance of the control switches. To abate or avoid this distortion, a "flip-over-capacitor" scheme may be used. By flipping over each capacitor to either an input or output node, four gain settings can be achieved. In one embodiment, the four gain settings are 0 dB, 3 dB, 9 dB, and 15 dB.

With reference to FIG. 9, the DC biasing points of the PGA 54 can be regulated by a fully balanced pseudo-resistor $R_{pseudo}$ with a fixed resistance. $R_{pseudo}$ is large enough to ensure that the resultant high-pass corner frequency is lower than the lowest high-pass corner frequency of the LNA 52. To ensure enough driving capability for the following Δ-ΔΣ ADC 50, in an embodiment, the transconductor $G_{m2}$ 68 for the PGA 54 has a buffer. The bias currents for the transconductor $G_{m2}$ 68 are mostly concentrated on the buffer. To provide enough phase margin and minimize the change of the high-frequency corner for the different gain setting, the compensation capacitors may also be selectable according to gain setting as shown in FIG. 10. The power consumption of the PGA 54 in one embodiment is 0.42 $\mu$W. Returning to FIG. 7, the AFE architecture 34 includes a Δ-ΔΣ ADC 50 comprising a Δ-modulator 46 and a ΔΣ ADC 48. The Δ-modulator 46 and a ΔΣ ADC 48 can operate with integration and feedback which does not impose a large area consumption when implementing AFE architectures. In the illustrated example, a first order ΔΣ ADC with a 32 oversampling ratio (OSR) can achieve greater than 10-bit resolution with the Δ-modulator 46 providing about 27 dB DR compression.

Again, returning to FIG. 7, the illustrated Δ-ΔΣ ADC 50 consists of two transconductance cells, $G_{m3}$ 70 and $G_{m4}$ 72. The Δ-ΔΣ ADC 50 also includes two digital-to-analog converters (DACs) and a 1-bit quantizer (e.g., a dynamic comparator 74). The DAC in the Δ-ΔΣ ADC 50 is implemented with NMOS switches, passives, and references.

Figure 11:
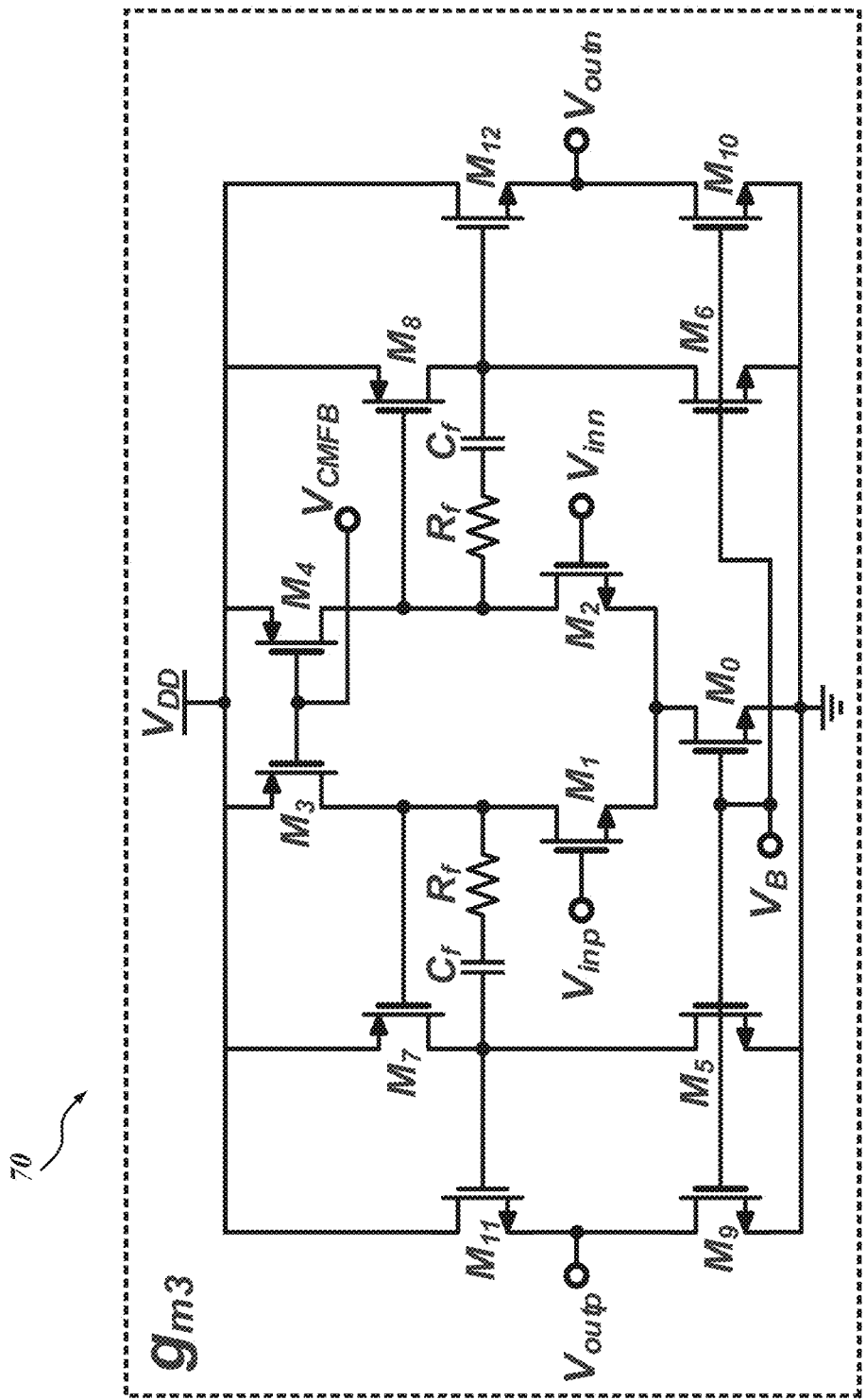
FIG. 11 is a schematic diagram of a first transconductor $G_{m3}$ in a continuous time (CT) $\Delta$-$\Delta\Sigma$ ADC.

FIG. 11 is a schematic diagram of one embodiment of the transconductor $G_{m3}$ 70 according to one embodiment of the CT Δ-ΔΣ ADC 50. The second transconductor $G_{m4}$ 72 is a simple, single-stage OTA, and thus a separate schematic is not provided. The gain, bandwidth, and DR requirement of the transconductor $G_{m3}$ 70 is typically more stringent than the requirements of $G_{m4}$ 72 since the first integrator using the transconductor $G_{m3}$ 70 should generate a delayed replica of the input signals with precision of over 60 dB SNR. In this particular embodiment, the transconductor $G_{m3}$ 70 consists of three stages with Miller compensation using passives, $C_f$ and $R_f$. The last stage is a buffer to drive the second integrator.

Figure 12:
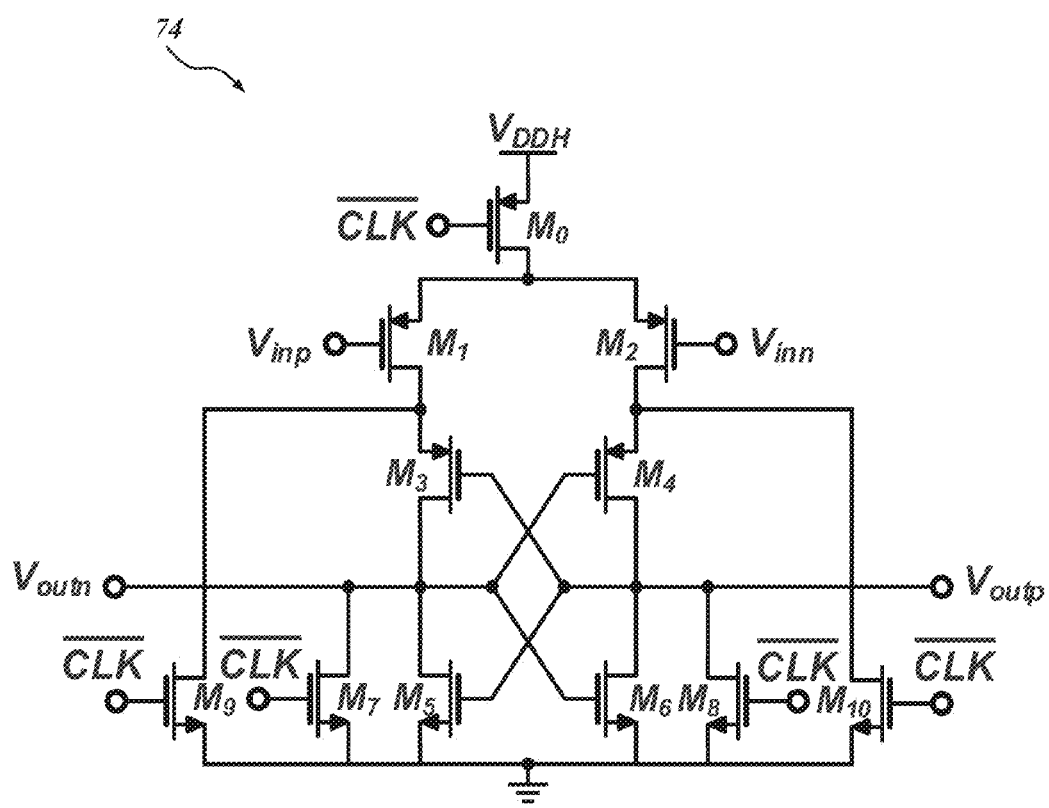
FIG. 12 is a schematic diagram of a dynamic comparator used as a 1-bit quantizer for a $\Delta$-$\Delta\Sigma$ ADC.

FIG. 12 is a schematic diagram of one embodiment of the dynamic comparator 74 in one implementation of the CT Δ-ΔΣ ADC 50. The comparator 74 can be used for the 1-bit quantization. In this embodiment, a 1 V power supply ($V_{DDH}$) is used since it is possible for a 0.5 V supply to make the decision time of the comparator slow. Consequently, it is possible for a 0.5 V supply, in some embodiments, to deteriorate the overall performance without an excess-loop-delay (ELD) compensation circuit. To minimize the effort involved with the assembly of the whole system, it is preferable that the data from all 128 channels is serialized onto 1-bit. However, it is possible for the 1-bit serialization to make the total output data rate of all 128 channels with $f_s$=800 kHz to become over 100 Mb/s, which can result in high power consumption for the data transmission. Accordingly, it is preferable, although not necessary, to implement on-chip decimation filters 56 for each individual channel to reduce the data rate, despite their possible additional area overhead. Additionally, it is possible to replace the 1-bit ΔΣ ADC 48 with a multi-bit ADC for further reduction of the area and energy consumption. A data-weighted averaging (DWA) block would likely be required in such an implementation to achieve the high linearity of the feedback block of the proposed Δ-ΔΣ ADC 50.

Figure 13:
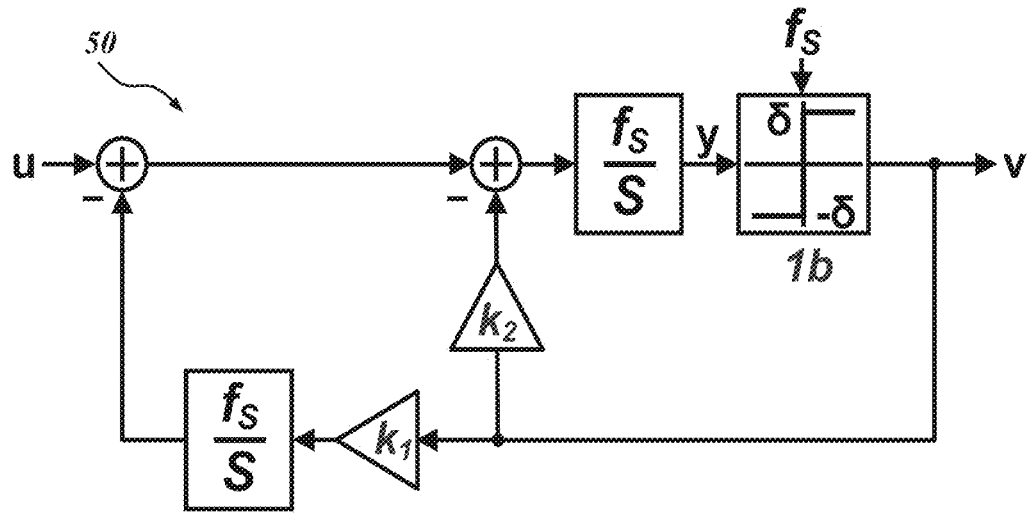
FIG. 13 is a block diagram of a CT $\Delta$-$\Delta\Sigma$ ADC.
Figure 14:
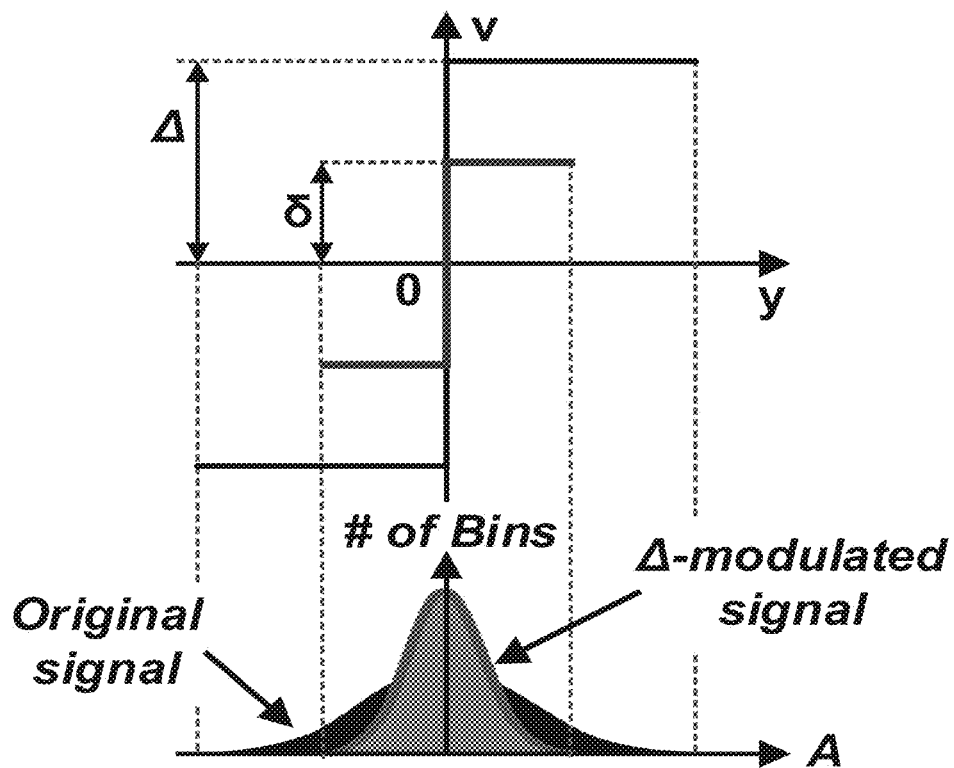
FIG. 14 shows a modified quantizer inside of the CT $\Delta$-$\Delta\Sigma$ ADC of FIG. 14.

FIG. 13 shows a block diagram of a proposed CT Δ-ΔΣ ADC 50 where the Δ-modulator 46 is cascaded with the ΔΣ ADC 48. In one embodiment, the structure of the Δ-modulator is a first order, and the ΔΣ modulator has a first order, single loop, feedback architecture with a single-bit quantizer. The feedback DACs are realized with non-return-zero (NRZ) signals. The feedback coefficients, k1 and k2 are determined as 1 and 1.5 by applying the inverse invariant transformation (ITT) to the discrete second order ΔΣ ADC 48 with the NRZ feedback waveform. Even though the loop filter looks like second order, as shown in FIG. 14, the overall noise transfer function (NTF) of the Δ-ΔΣ ADC 50 is the same as the first order ΔΣ modulator considering off-chip integration (e.g., with Σ modulation) to restore the original input signals. However, compared to the first order ΔΣ modulator, the quantization step is much smaller since it is typically just the prediction error from the Δ-modulator 46.

Figure 15:
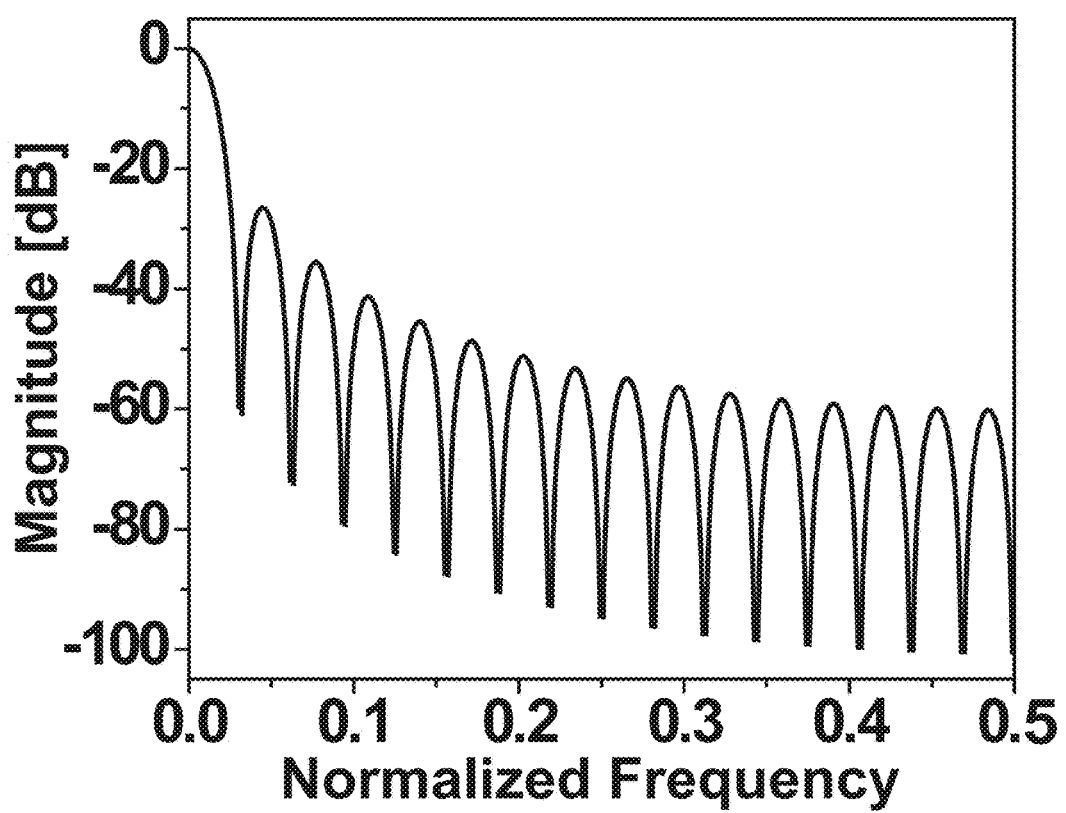
FIG. 15 is a graph illustrating the frequency response of a $sinc^2$ filter for the decimation of the output of the $\Delta$-$\Delta\Sigma$ ADC.

With reference to FIG. 14, in one implementation of a CT Δ-ΔΣ ADC 50, the quantization step is bounded by δ within the maximum derivative of the input signal times the sampling interval ($T_s$=1/$f_s$). As shown in FIG. 15, quantization noise becomes smaller, and thus a lower noise floor coming from the quantization process can be achieved.

FIG. 15 is a graph illustrating the frequency response of a $sinc^2$ filter for the decimation of the output of the Δ-ΔΣ ADC 50. Since in one embodiment, the overall noise transfer function of the off-chip signal restoration is the first order, a $sinc^2$ filter is able to provide enough attenuation of the out-band noise. Equation 6 below shows the transfer function of the second order sinc filter:

$$H(e^{j2\pi f}) = \left(\frac{sinc(Nf)}{sinc(f)}\right)^2 \quad \text{(equation 5)}$$

where f and N are the normalized frequency and number of taps (32 by the OSR of the Δ-ΔΣ ADC 50). The $sinc^2$ filter can be implemented using auto-place and routing (APR) and may be designed such that it occupies an area of only 0.00288 mm² (40 μm×72 μm).

Figure 16:
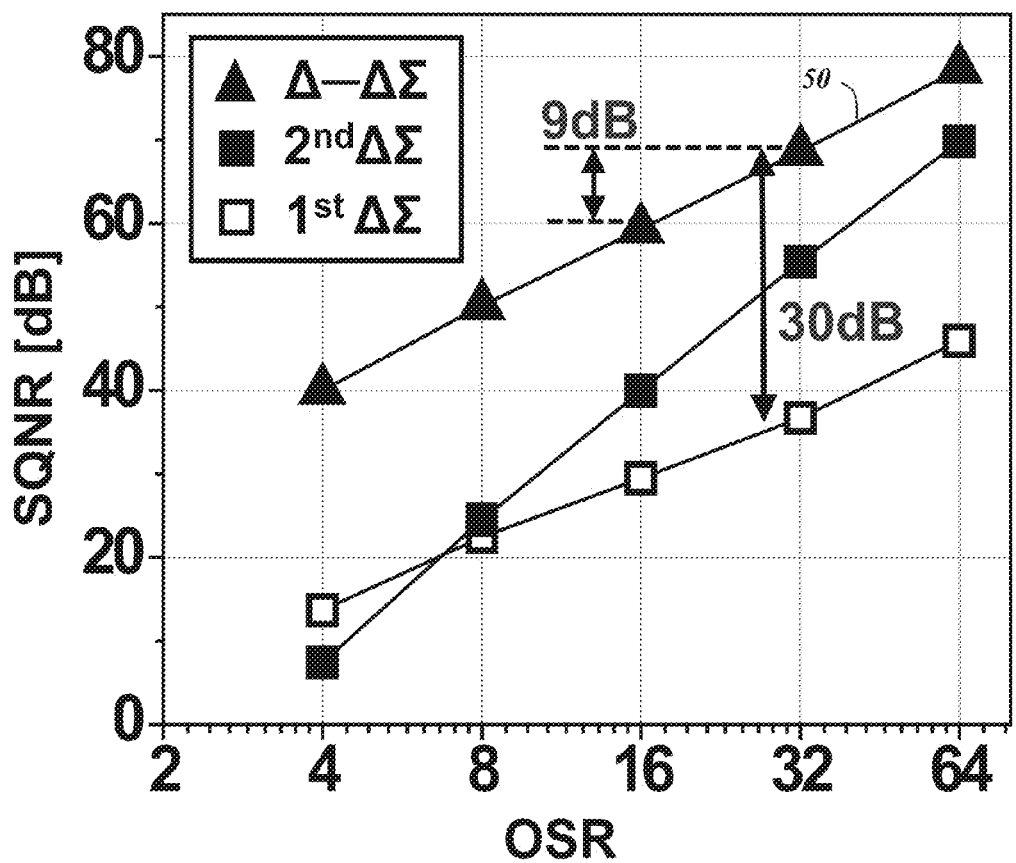
FIG. 16 is a graph illustrating the signal-to-quantization-noise ratio (SQNR) of first and second order $\Delta\Sigma$, and $\Delta$-$\Delta\Sigma$ ADC for different over-sampling ratios (OSR)

FIG. 16 shows a numerical simulation for the signal to quantization noise ratio (SQNR) of a first order and second order ΔΣ modulator, and a Δ-ΔΣ ADC 50 by changing the OSR from 4 to 64. For the Δ-ΔΣ ADC 50 and ΔΣ ADC 48, δ=0.025 and Δ=1 are used, respectively. As indicated, the slope of the SQNR improvement is about the same for the first order ΔΣ modulator (+9 dB by doubling the OSR) and the Δ-ΔΣ ADC 50. However, the Δ-ΔΣ ADC 50 has about a 30 dB offset compared to the first order ΔΣ modulator which is at least partly attributable to the reduced quantization noise. The SQNR may be even further improved if the energy of input signal is bounded within a smaller bandwidth.

Figure 17:
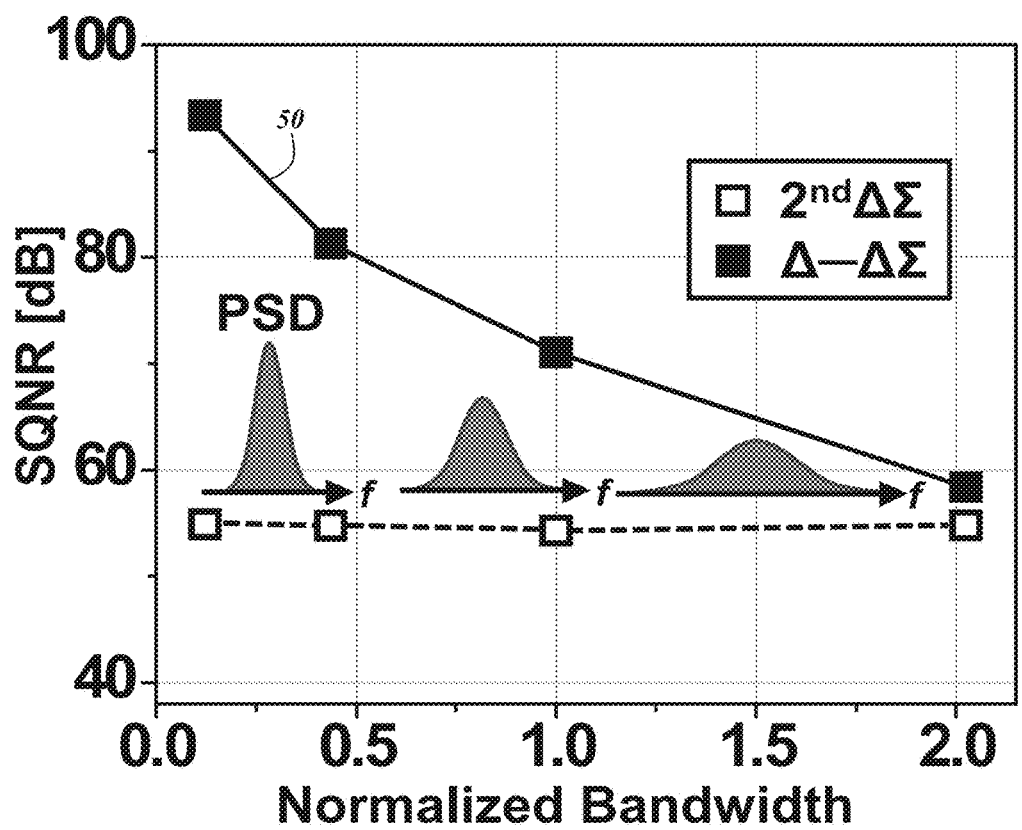
FIG. 17 is a graph illustrating the SQNR of a second order $\Delta\Sigma$ modulator and a $\Delta$-$\Delta\Sigma$ ADC for different bandwidth signals.
Figure 18:
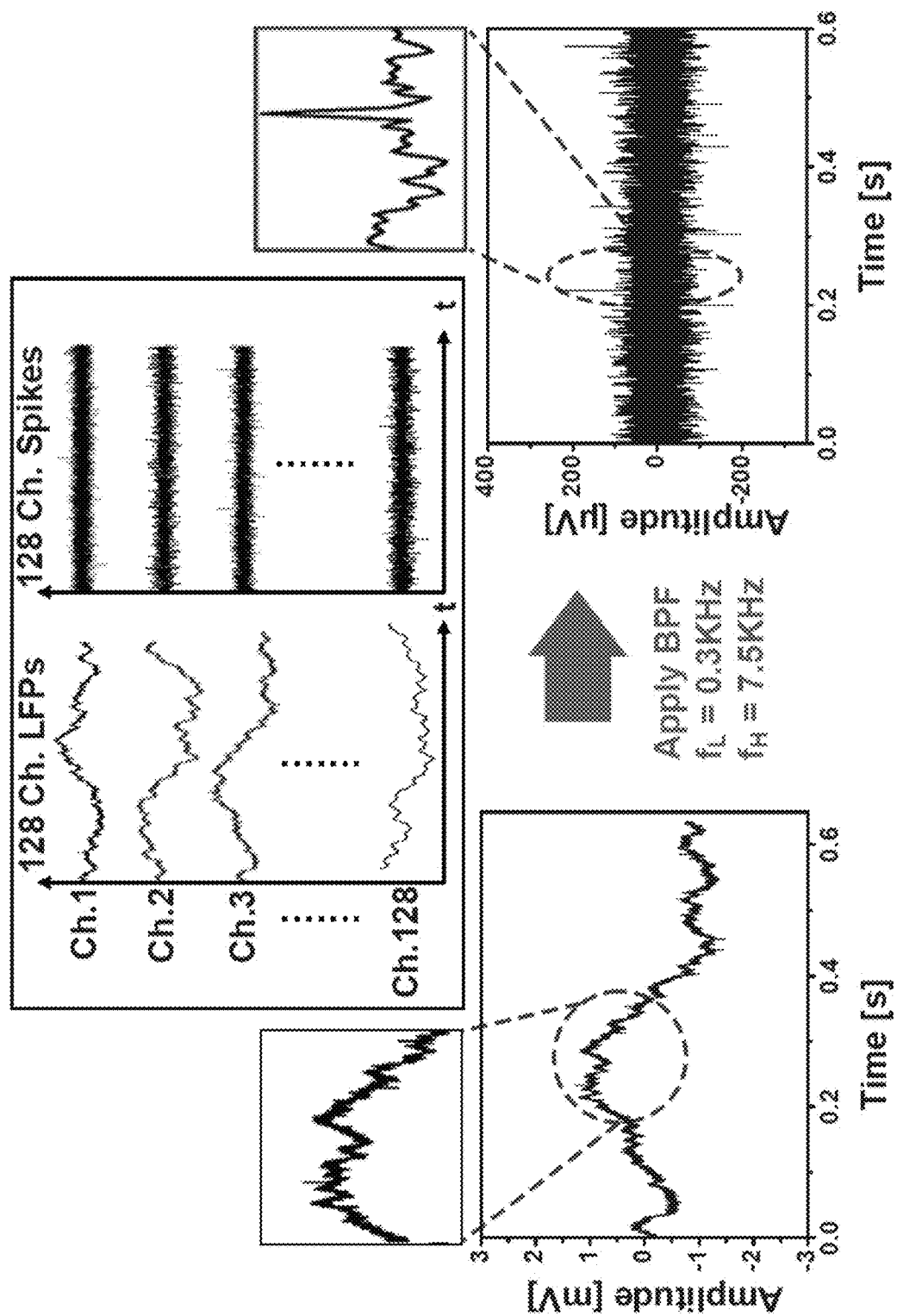
FIG. 18 shows in vivo measurement of local field potentials (LFPs) and bandpass filtered action potentials (APs) using a biological recording device according to one embodiment.

FIG. 17 shows another numerical simulation (fixed OSR=32) with four input signals. The input signals have different bandwidths, but the total energies are the same. To aid understanding, the conceptual power spectral densities (PSDs) are also depicted in FIG. 18. While the SQNR of the second order ΔΣ modulator remains same, that of the Δ-ΔΣ ADC 50 becomes higher as the bandwidth of the signal decreases. This characteristic is particularly advantageous for neural signals including LFPs whose energy is mostly located low-frequency region (e.g., less than about 600 Hz) and APs which have a higher bandwidth with small energy. The first order Δ-ΔΣ ADC 50 with a 32 over-sampling ratio (OSR) and 800 kHz can achieve over 10-bit resolution in this architecture with the aid of an additional 30 dB improvement from the Δ-modulator 46.

Figure 19:
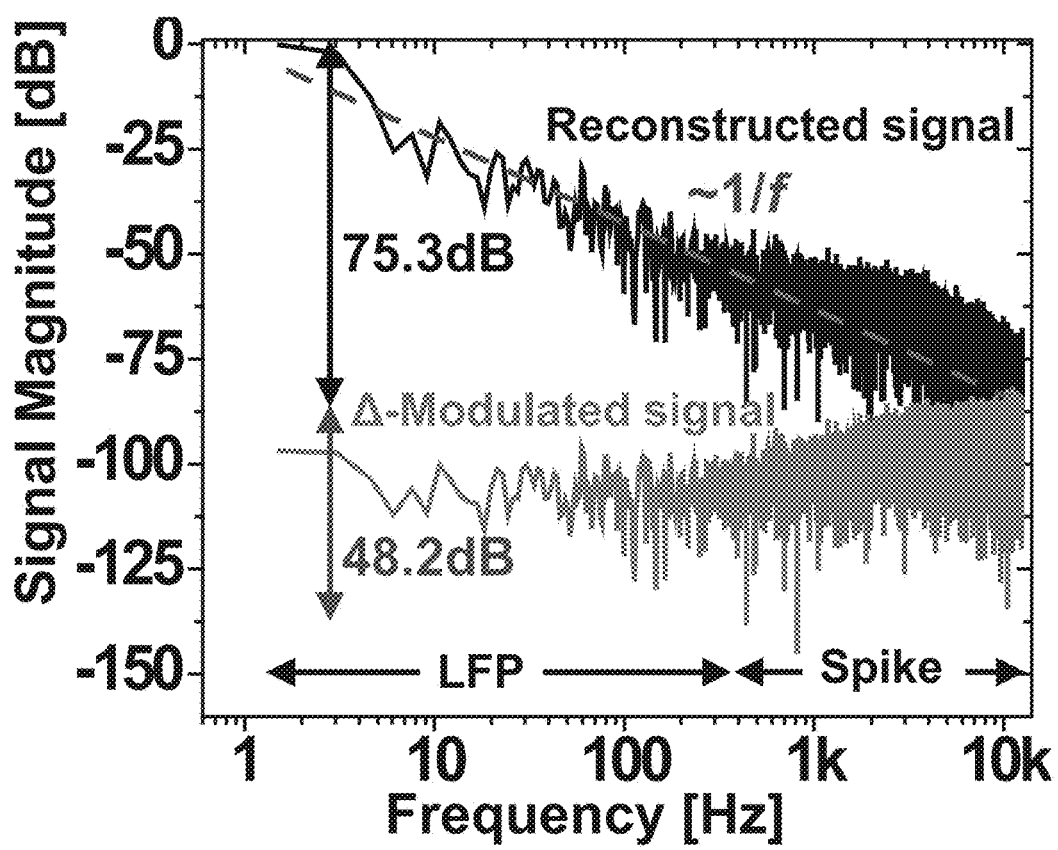
FIG. 19 is a graph illustrating power spectra of recorded and reconstructed neural signals.
Figure 20:
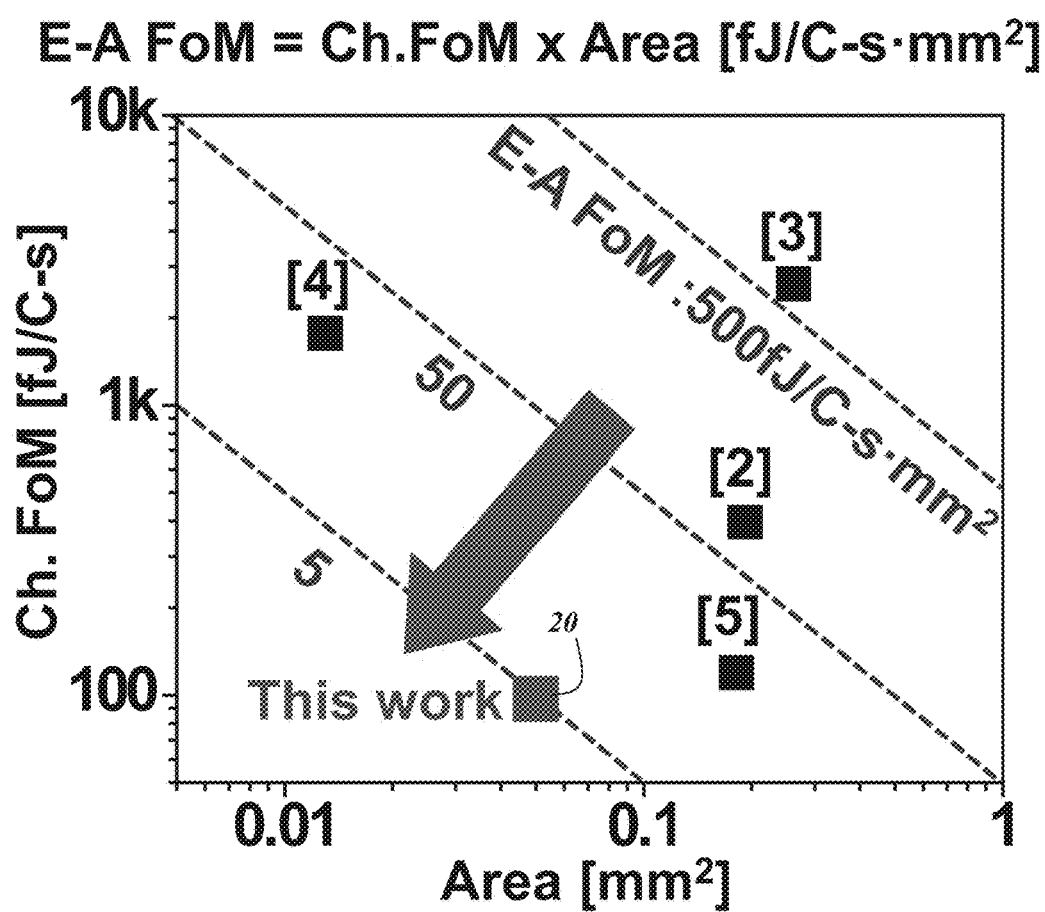
FIG. 20 compares energy-area figures of merit (FoM) for various biological recording devices.

FIGS. 18-24 illustrate various performance data and signal processing results for a fabricated neural probe biological recording device 20. FIG. 18 shows in-vivo measurements from the neo-cortex of a rodent using a multi-shank biological recording device 20. The left plot shows the raw signals, where spikes (~200 μV) are superimposed on large LFP fluctuations (~1.2 mV). The right plot shows only the spikes after band-pass filtering. The 128-channel recordings are shown in the center. FIG. 19 shows the power spectra of compressed and reconstructed neural signals. As expected, the raw signal exhibits a ~1/f slope. The 75.3 dB full-DR is modulated into 48.2 dB. Accordingly, about 27 dB compression is achieved. FIG. 20 is a plot showing the energy-area figure of merit of the biological recording device 20 compared with prior art devices labeled [2]-[5] in the drawing. The biological recording device 20 achieves the best energy-area figure of merit of 4.84 fJ/C-s*mm². The next highest energy-area figure of merit is 21.28 fJ/C-s*mm².

Figure 21:
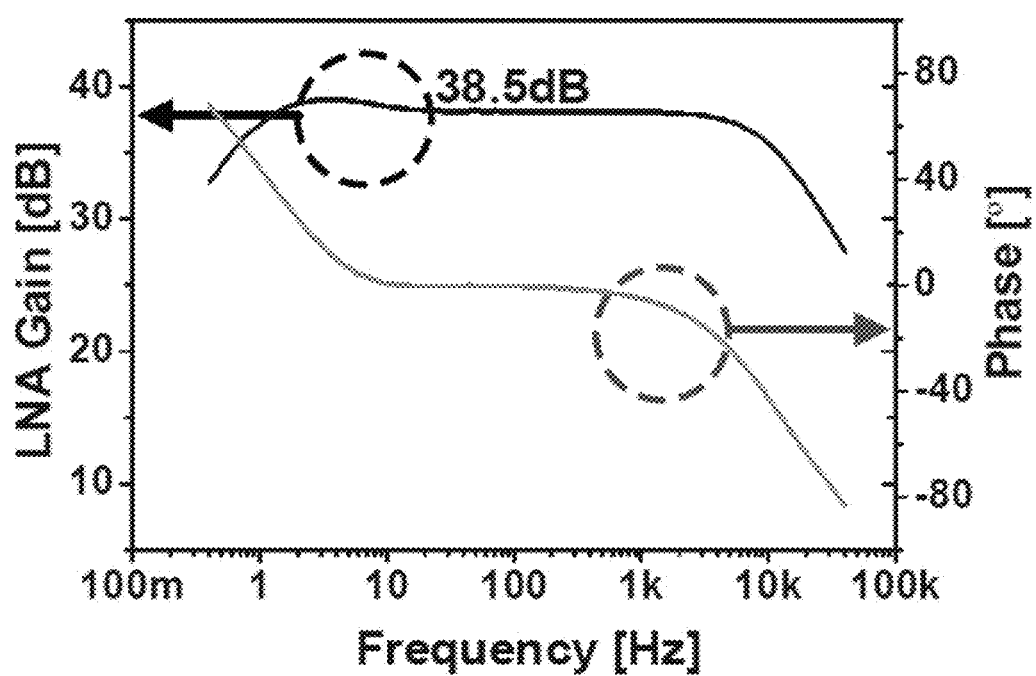
FIG. 21 is a graph illustrating LNA gain over various frequencies.
Figure 22:
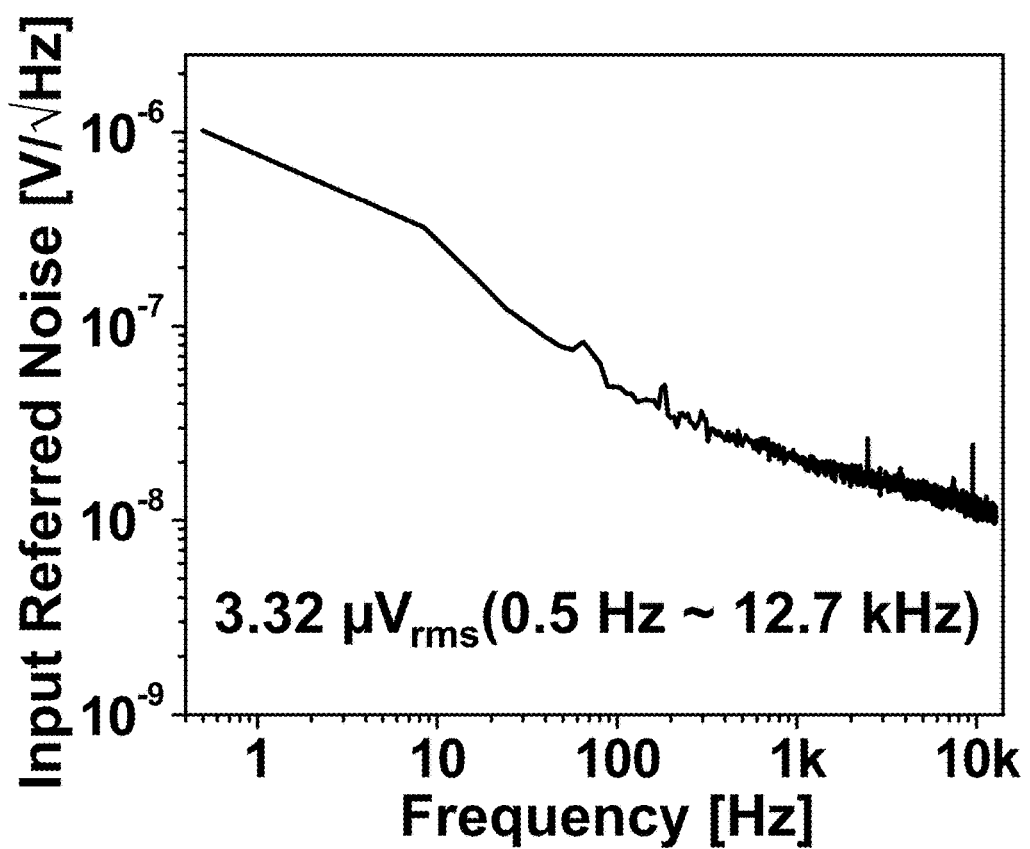
FIG. 22 is a graph illustrating input referred noise over various frequencies.
Figure 23:
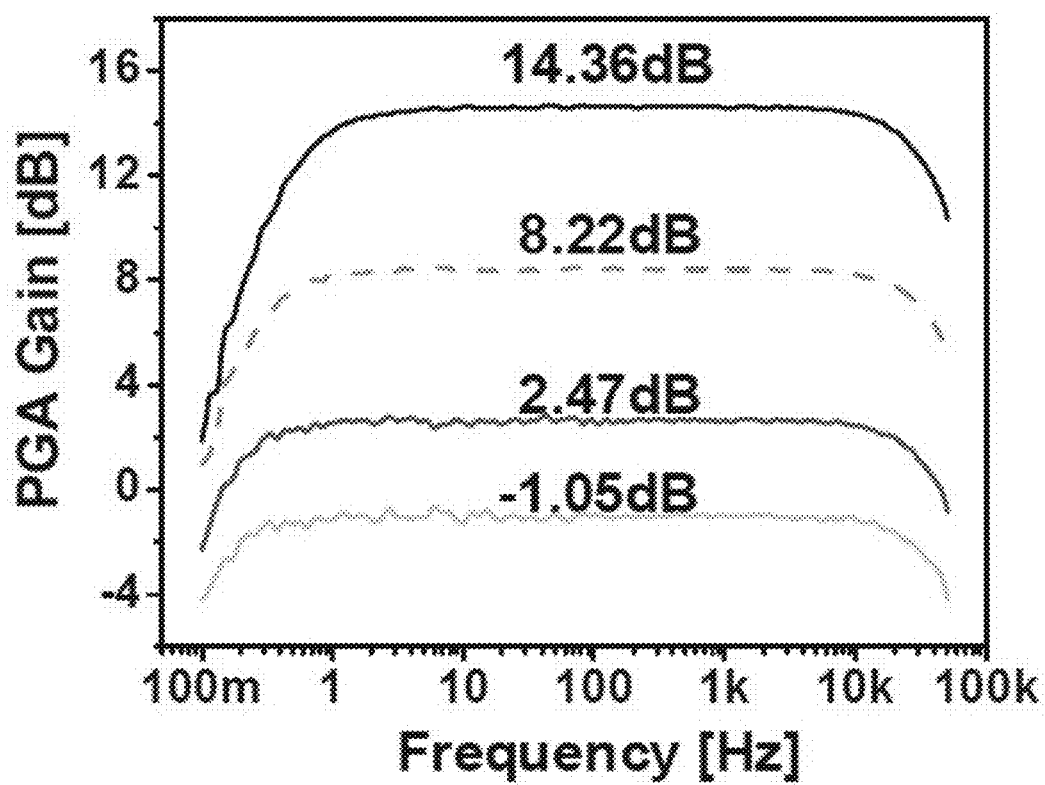
FIG. 23 is a graph illustrating PGA gain over various frequencies.
Figure 24:
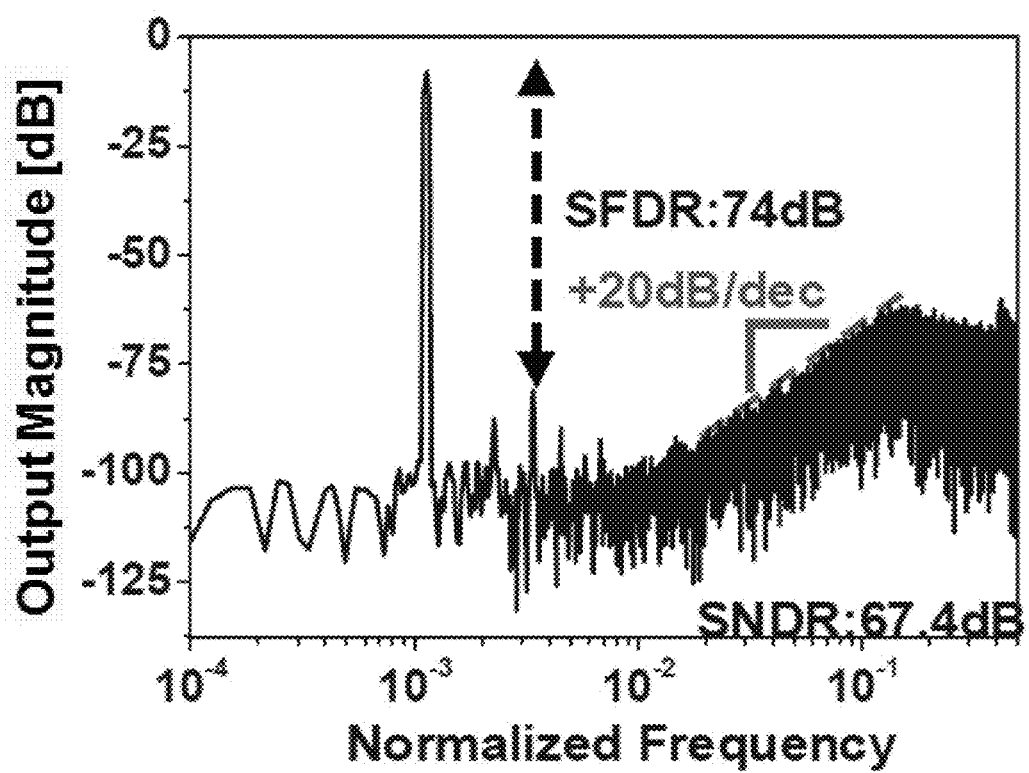
FIG. 24 is a graph showing measured characteristics of a ΔΣ ADC.

FIGS. 21-24 show measured characteristics of the LNA 52, PGA 54, and ΔΣ ADC 48 of the biological recording device 20. With reference to FIGS. 21 and 22, the LNA 52 has a gain of about 38.5 dB from about 0.4 Hz to 10.9 kHz with 3.32 $μV_{rms}$ input-referred noise. FIG. 23 shows that the PGA 54 generates four different gains: about −1 dB, 2.5 dB, 8.2 dB, and 14.4 dB. FIG. 25 shows that the SFDR and SNDR of the ΔΣ ADC 48 are about 74 dB and 67.4 dB (10.9-bit ENOB), respectively. The ADC can consume about 1.68 μW and its energy figure of merit is about 35.2 fJ/C-s.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A biological recording device, comprising:
a probe body having a probe shank;
a plurality of recording electrodes on the probe shank for monitoring a dynamic range of biological electrical activity, wherein one or more of the recording electrodes have an energy-area product between 4.84 fJ/C-s*mm$^2$ and 21.27 fJ/C-s*mm$^2$, inclusive; and
a recording platform attached to the probe body for processing the biological electrical activity monitored by the plurality of recording electrodes, wherein the recording platform includes a delta ($\Delta$) modulator and the dynamic range of the biological electrical activity is modulated by the $\Delta$ modulator.

2. The biological recording device of claim 1, wherein the recording platform further comprises a delta sigma analog-to-digital converter ($\Delta\Sigma$ ADC) and the $\Delta$ modulator and the $\Delta\Sigma$ ADC comprise a $\Delta$-$\Delta\Sigma$ analog front-end (AFE) architecture.

3. The biological recording device of claim 2, wherein the dynamic range of the biological electrical activity is modulated by the $\Delta$ modulator before it is digitized by the $\Delta\Sigma$ ADC.

4. The biological recording device of claim 2, wherein the $\Delta$-$\Delta\Sigma$ AFE architecture is bonded on an interposer which interconnects the $\Delta$-$\Delta\Sigma$ AFE architecture and the probe body.

5. The biological recording device of claim 2, wherein the $\Delta$-$\Delta\Sigma$ AFE architecture uses continuous time (CT) quantization.

6. The biological recording device of claim 2, further comprising a capacitive coupling that includes a plurality of capacitors placed adjacent to the $\Delta$-$\Delta\Sigma$ AFE architecture.

7. The biological recording device of claim 2, further comprising a low-noise amplifier (LNA), a programmable gain amplifier (PGA), and a decimation filter, wherein the LNA, the PGA, the $\Delta$ modulator, the $\Delta\Sigma$ ADC and the decimation filter are connected in series.

8. The biological recording device of claim 1, wherein each recording electrode monitors biological electrical activity and transmits a signal representative of the biological electrical activity via a channel to the recording platform.

9. The biological recording device of claim 8, wherein a plurality of signals representative of the biological electrical activity are multiplexed in the digital domain.

10. The biological recording device of claim 1, wherein the biological electrical activity is serialized into a single bit.

11. The biological recording device of claim 1, further comprising a plurality of probe shanks that extend from the probe body.

12. The biological recording device of claim 11, further comprising a plurality of recording platforms, each recording platform being attached to a respective one of a plurality of probe bodies.

13. A biological recording device, comprising:
a probe body having a probe shank;
a plurality of recording electrodes on the probe shank for monitoring biological electrical activity, wherein one or more of the recording electrodes have an energy-area product between 4.84 fJ/C-s*mm$^2$ and 21.27 fJ/C-s*mm$^2$, inclusive; and
a recording platform attached to the probe body for processing the biological electrical activity monitored by the plurality of recording electrodes, wherein the recording platform includes a delta sigma analog to digital converter ($\Delta\Sigma$ ADC) to digitize the biological electrical activity.

14. A method of processing neural signals using the biological recording device of claim 13, the method comprising the steps of:
acquiring a dynamic range for a plurality of neural signals;
compressing the dynamic range for the plurality of neural signals; and
quantizing the compressed dynamic range for the plurality of neural signals using the delta sigma analog to digital converter ($\Delta\Sigma$ ADC).

15. The method of claim 14, further comprising the step of reconstructing the quantized dynamic range for the plurality of neural signals through sigma-modulated integration to obtain a retrieved dynamic range representing the plurality of neural signals.

16. The method of claim 14, wherein the compressing step includes delta ($\Delta$) modulating that takes a temporal difference of oversampled neural signals.

17. The method of claim 14, wherein the quantizing step operates in continuous time (CT).

18. The method of claim 14, wherein the plurality of neural signals includes local field potentials (LFPs) and action potentials (APs) that are monitored simultaneously.

19. A biological recording device, comprising:
a probe body having a probe shank;
a plurality of recording electrodes on the probe shank for monitoring a dynamic range of biological electrical activity; and
a recording platform attached to the probe body for processing the biological electrical activity monitored by the plurality of recording electrodes, wherein the recording platform includes a delta ($\Delta$) modulator and a delta sigma analog-to-digital converter ($\Delta\Sigma$ ADC), wherein the $\Delta$ modulator is configured to modulate the dynamic range of the biological electrical activity before being digitized by the $\Delta\Sigma$ ADC.

* * * * *